US010300252B2

(12) United States Patent
Lee et al.

(10) Patent No.: US 10,300,252 B2
(45) Date of Patent: May 28, 2019

(54) DEVICES AND METHODS FOR TREATING ACUTE KIDNEY INJURY

(71) Applicant: RenalPro Medical, Inc., San Jose, CA (US)

(72) Inventors: Tsung-Chun Lee, New Taipei (TW); Wen-Pin Shih, Taipei (TW)

(73) Assignee: RenalPro Medical, Inc., Palo Alto, CA (US)

( * ) Notice: Subject to any disclaimer, the term of this patent is extended or adjusted under 35 U.S.C. 154(b) by 354 days.

(21) Appl. No.: 15/189,460

(22) Filed: Jun. 22, 2016

(65) Prior Publication Data

US 2016/0375230 A1 Dec. 29, 2016

Related U.S. Application Data

(63) Continuation of application No. PCT/US2014/072302, filed on Dec. 23, 2014.
(Continued)

(51) Int. Cl.
*A61M 29/00* (2006.01)
*A61M 25/10* (2013.01)
(Continued)

(52) U.S. Cl.
CPC ..... *A61M 25/1011* (2013.01); *A61B 17/1204* (2013.01); *A61B 17/12109* (2013.01);
(Continued)

(58) Field of Classification Search
CPC .............. A61M 1/1072; A61M 1/1001; A61M 1/1008; A61M 1/101; A61M 1/1034; A61M 1/1056; A61M 1/106; A61M 1/1086; A61M 1/12; A61M 1/122; A61M 1/125; A61M 2025/0002; A61M 2025/0073; A61M 2025/1052; A61M 2025/1079; A61M 2025/1095; A61M 2205/32; A61M 2205/3327; A61M 2210/1082;
(Continued)

(56) References Cited

U.S. PATENT DOCUMENTS 5,879,499 A 3/1999 Corvi
6,036,697 A 3/2000 DiCaprio
(Continued)

FOREIGN PATENT DOCUMENTS

CN 201692487 U 1/2011
EP 1379185 A1 1/2004
(Continued)

OTHER PUBLICATIONS

Bourouina et al. Design and simulation of an electrostatic micropump for drug-delivery applications. Journal of Micromechanics and Microengineering, 7(3):186, Jan. 1999.
(Continued)

*Primary Examiner* — Jason E Flick
(74) *Attorney, Agent, or Firm* — Wilson Sonsini Goodrich & Rosati

(57) ABSTRACT

A catheter devices/systems and methods therefrom are described herein for treating acute kidney injury, especially the contrast-induced acute kidney injury wherein the devices prevent the contrast dyes from entering into kidney and/or facilitate blood flow of kidney by said catheter system.

12 Claims, 18 Drawing Sheets

Related U.S. Application Data

(60) Provisional application No. 62/011,034, filed on Jun. 12, 2014, provisional application No. 61/921,197, filed on Dec. 27, 2013.

(51) Int. Cl.
  *A61B 17/12* (2006.01)
  *A61M 5/00* (2006.01)
  *A61M 25/00* (2006.01)
  *A61M 1/10* (2006.01)
  *A61M 1/12* (2006.01)

(52) U.S. Cl.
  CPC ....... *A61B 17/12136* (2013.01); *A61M 5/007* (2013.01); *A61M 1/1001* (2014.02); *A61M 1/101* (2013.01); *A61M 1/106* (2013.01); *A61M 1/1008* (2014.02); *A61M 1/1034* (2014.02); *A61M 1/1056* (2014.02); *A61M 1/1072* (2013.01); *A61M 1/1086* (2013.01); *A61M 1/12* (2013.01); *A61M 1/122* (2014.02); *A61M 1/125* (2014.02); *A61M 2025/0002* (2013.01); *A61M 2025/0073* (2013.01); *A61M 2025/1052* (2013.01); *A61M 2025/1079* (2013.01); *A61M 2025/1095* (2013.01); *A61M 2205/32* (2013.01); *A61M 2205/3327* (2013.01); *A61M 2210/1082* (2013.01); *A61M 2210/12* (2013.01)

(58) Field of Classification Search
  CPC .......... A61M 2210/12; A61M 25/1011; A61M 5/007; A61B 17/12109; A61B 17/1204; A61B 17/12136; A61B 17/12036; A61B 2090/063; A61B 2090/064
  USPC .................................................... 604/101.01
  See application file for complete search history.

(56) References Cited

U.S. PATENT DOCUMENTS

| | | | |
|---|---|---|---|
| 6,251,093 B1 | 6/2001 | Valley et al. | |
| 6,287,315 B1 * | 9/2001 | Wijeratne | A61B 17/12109 606/108 |
| 6,638,293 B1 | 10/2003 | Makower et al. | |
| 6,692,484 B1 | 2/2004 | Karpiel et al. | |
| 6,767,345 B2 | 7/2004 | St. Germain et al. | |
| 6,913,600 B2 | 7/2005 | Valley et al. | |
| 7,063,679 B2 | 6/2006 | Maguire et al. | |
| 7,766,892 B2 * | 8/2010 | Keren | A61M 1/3653 604/509 |
| 9,861,794 B2 | 1/2018 | Ringvad et al. | |
| 2002/0169413 A1 | 11/2002 | Keren et al. | |
| 2003/0212361 A1 | 11/2003 | Boyle et al. | |
| 2004/0059179 A1 | 3/2004 | Maguire et al. | |
| 2004/0097900 A1 | 5/2004 | Keren et al. | |
| 2005/0148997 A1 | 7/2005 | Valley et al. | |
| 2005/0203553 A1 | 9/2005 | Maschke | |
| 2005/0203558 A1 | 9/2005 | Maschke | |
| 2006/0149350 A1 | 7/2006 | Patel et al. | |
| 2011/0034948 A1 | 2/2011 | Ravikumar | |
| 2011/0282274 A1 | 11/2011 | Fulton, III et al. | |
| 2013/0123621 A1 | 5/2013 | Isham et al. | |
| 2013/0245552 A1 | 9/2013 | Ogle et al. | |
| 2014/0051968 A1 | 2/2014 | Isham et al. | |
| 2015/0094609 A1 * | 4/2015 | Jacobson | A61F 5/08 600/549 |
| 2018/0250015 A1 | 9/2018 | Koo et al. | |

FOREIGN PATENT DOCUMENTS

| | | |
|---|---|---|
| WO | WO-9640347 A1 | 12/1996 |
| WO | WO-0025851 A1 | 5/2000 |
| WO | WO-2009052838 A1 | 4/2009 |
| WO | WO-2010018569 A1 | 2/2010 |
| WO | WO-2015100393 A1 | 7/2015 |
| WO | WO-2017192912 A1 | 11/2017 |

OTHER PUBLICATIONS

Huang et al. Pneumatic micropumps with serially connected actuation chambers. Journal of Micromechanics and Microengineering, 16(11):2265, Sep. 2006.

Zhang et al. Study on an alternating current electrothermal micropump for microneedle-based fluid delivery systems. Journal of Applied Physics, 114(2), Jul. 2013.

Du, et al., ZnO film based surface acoustic wave micro-pump, J of Physics; Conference Series, 2007, 012047, Abstract.

Extended European Search Report and Search Opinion dated Dec. 6, 2017 for European Patent Application No. EP14875849.3.

International search report and written opinion dated May 28, 2015 for PCT Application No. US-2014072302.

International Search Report and Written Opinion dated Jul. 20, 2017 for International PCT Patent Application No. PCT/US2017/031153.

"Office action dated Nov. 6, 2018 for U.S. Appl. No. 15/969,050.".

\* cited by examiner

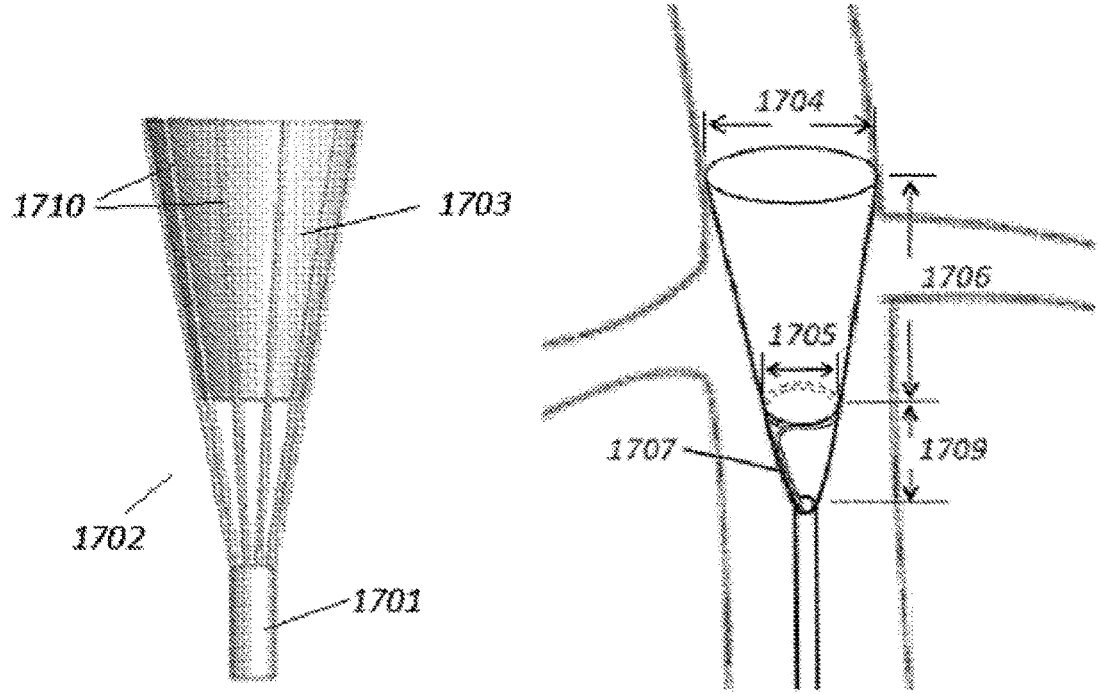
FIG. 17A
FIG. 17B
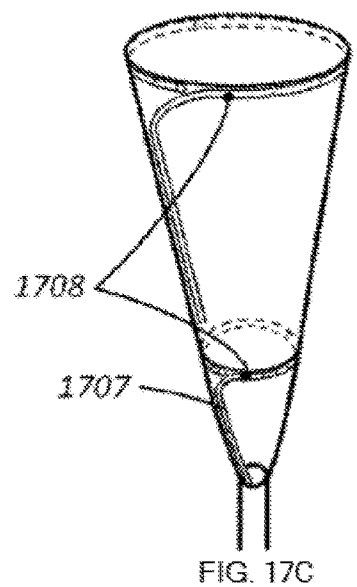
FIG. 17C

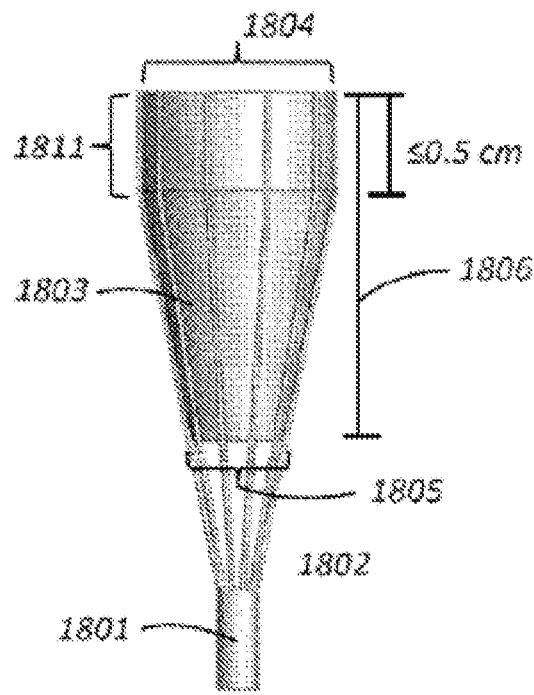
FIG. 18A
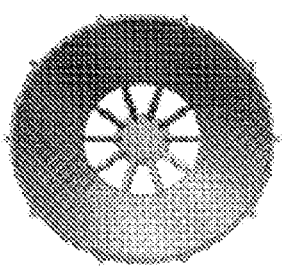 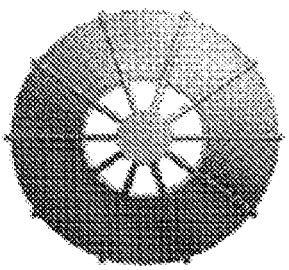
FIG. 18B  FIG. 18C
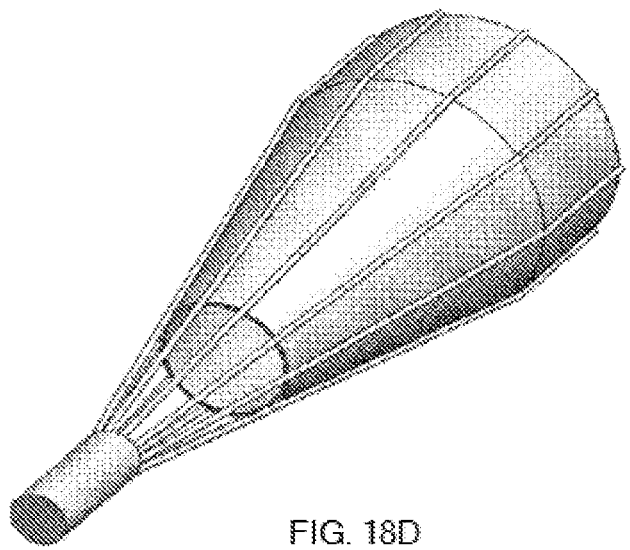
FIG. 18D

DEVICES AND METHODS FOR TREATING ACUTE KIDNEY INJURY

BACKGROUND OF THE INVENTION

Acute kidney injury (AKI), also called acute renal failure (ARF), is a rapid loss of kidney function. Its causes are numerous and include low blood volume from any cause, exposure to substances harmful to the kidney, and obstruction of the urinary tract. AKI is diagnosed on the basis of characteristic laboratory finding, such as elevated blood creatinine, or inability of the kidneys to produce sufficient amounts of urine.

Acute kidney injury is diagnosed on the basis of clinical history and laboratory data. A diagnosis is made when there is rapid reduction in kidney function, as measured by serum creatinine, or based on a rapid reduction in urine output, termed oliguria.

For example, the use of intravascular iodinated contrast agents may cause acute kidney injury. In patients receiving intravascular iodine-containing contrast media for angiography, contrast-induced AKI (CI-AKI) is a common problem and is associated with excessive hospitalization cost, morbidity, and mortality. Clinical procedures involving intravascular iodine-containing contrast media injection include for example, percutaneous coronary intervention (PCI), peripheral vascular angiography and intervention, neurological angiography and intervention. In clinical practice, when an increase of serum creatinine by more than 25% or 0.5 mg/dL from baseline level, without other culprit etiology for AKI within 48 to 72 hours of exposure to contrast media, the diagnosis of CI-AKI is usually made.

The management of AKI hinges on identification and treatment of the underlying cause. In addition to treatment of the underlying disorder, management of AKI routinely includes the avoidance of substances that are toxic to the kidneys, called nephrotoxins. These include non-steroidal anti-inflammatory drugs (NSAIDs) such as ibuprofen, iodinated contrasts such as those used for CT scans, many antibiotics such as gentamicin, and a range of other substances.

Monitoring of renal function, by serial serum creatinine measurements and monitoring of urine output, is routinely performed. In the hospital, insertion of urinary catheter helps monitor urine output and relieves possible bladder outlet obstruction, such as with an enlarged prostate. In prerenal AKI without fluid overload, administration of intravenous fluids is typically the first step to improve renal function. Volume status may be monitored with the use of a central venous catheter to avoid over- or under-replacement of fluid. Should low blood pressure prove a persistent problem in the fluid-replete patient, inotropes such as norepinephrine and dobutamine may be given to improve cardiac output and enhance renal perfusion. Also, while a useful pressor, there is no evidence to suggest that dopamine is of any specific benefit, and may be harmful.

The myriad causes of intrinsic AKI require specific therapies. For example, intrinsic AKI due to Wegener's granulomatosis may respond to steroid medication. Toxin-induced prerenal AKI often responds to discontinuation of the offending agent, such as aminoglycoside, penicillin, NSAIDs, or paracetamol.

If the cause is obstruction of the urinary tract, relief of the obstruction (with a nephrostomy or urinary catheter) may be necessary.

Renal replacement therapy, such as with hemodialysis, may be instituted in some cases of AKI. A systematic review of the literature in 2008 shows no difference in outcomes between the use of intermittent hemodialysis and continuous venovenous hemofiltration (CVVH). Among critically ill patients, intensive renal replacement therapy with CVVH does not appear to improve outcomes compared to less intensive intermittent hemodialysis.

SUMMARY OF THE INVENTION

In one aspect provides a device for treating or reduce the risk of acute kidney injury, comprising: a balloon catheter having at least one balloon, at least one sensor associated with the balloon, and a disturbing means associated with the balloon, wherein the balloon with the disturbing means generates augmented renal blood flow to avoid renal ischemia and to dilute contrast media flow inside kidneys.

In another aspect provides a device for treating or reducing the risk of acute kidney injury, comprising: a balloon catheter having at least one balloon, at least one sensor associated with the balloon and a position indication means wherein the balloon occlude the orifice of both sides of renal arteries after inflation while allowing blood flow goes through the inflated balloon during application of the device inside abdominal aorta.

In another aspect of the present invention, there is provided a device for treating or reducing the risk of contrast-induced acute kidney injury, comprising: a catheter, a position indication means on the catheter, and a flow disturbing means retractable into the catheter wherein the flow disturbing means is positioned at suprarenal aorta to provide blood flow disturbance which makes a contrast media become diluted before taking into the renal arteries carrying by a disturbed blood flow distributing back to the infra-renal aorta.

In yet another aspect provides a method for treating or reducing the risk of contrast-induced acute kidney injury comprising
  inserting the catheter of claim 1 to abdominal aorta;
  placing the catheter at suprarenal aorta; and
  deploying the disturbing means at a position allowing the disturbing means to provide blood flow disturbance which makes a contrast media become diluted before taking into the renal arteries.

In certain aspect of the invention, the acute kidney injury is contrast-induced acute kidney injury. In certain embodiments, the device comprises a balloon catheter having a first balloon, a second balloon and at least one sensor associated with the second balloon. In some embodiments, the device comprises a balloon catheter having a first balloon, a second balloon and at least one sensor associated with the second balloon. In certain embodiments, the device further comprises a side aperture for infusing normal saline or medication. In certain embodiments, the medication is a vasodilatory agent. In certain embodiments, the vasodilatory agent is fenoldopam.

In some embodiments, the sensor is a pressure sensor. In certain embodiments, the pressure sensor measures the blood flow pressure. In some embodiments, the sensor is a size measuring sensor. In certain embodiments, the size measuring sensor measures the size of balloon. In certain embodiments, the device comprises two sensors. In certain embodiments, the device comprises a first sensor at upper side of the second balloon and a second sensor at lower side of the second balloon. In certain embodiments, the device comprises a first sensor at upper side of the second balloon and a second sensor at lower side of the second balloon. In certain embodiments, the sensor provides data for the control unit to control the size of the first and/or second balloons.

In some embodiments, the balloon catheter further includes a guidewire and a spinning propeller. In certain embodiments, the spinning propeller spins around the central guidewire to generate directional augmented renal artery blood flow toward the kidney. In certain embodiments, the spinning propeller is wing shape or fin shape. In certain embodiments, the device further comprises another catheter comprising a guidewire and a spinning propeller to generate directional augmented blood flow to the other kidney. In certain embodiments, the additional catheter having a spinning propeller is functioned independently and simultaneously with the balloon catheter to generate directional augmented blood flow to each side of kidney.

In another aspect, a method for treating contrast-induced acute kidney injury is disclosed. The method comprises: inserting the device comprising a balloon catheter having a first balloon, a second balloon, at least one sensor to abdominal aorta; placing the balloon catheter at a position allowing the first balloon at the supra-renal aorta position near orifices of bilateral renal arteries; inflating the first balloon to occlude the orifice of both sides of renal arteries during the application of contrast media; deflating the first balloon after the contrast media has completely employed; inflating the second balloon to the extent not totally occlude the aorta blood flow at the location of infra-renal aorta near the orifice of renal arteries; deflating the second balloon; and infusing normal saline and/or suitable medication via the side aperture into the supra-renal aorta.

In some embodiments, the insertion of the device to abdominal aorta is applied either by transfemoral artery approach or by trans-brachial artery approach or by trans-radial artery approach. In certain embodiments, the balloon catheter further includes a guidewire and a spinning propeller. In certain embodiments, the method further comprises inserting a guidewire into renal artery. In certain embodiments, the method further comprises inserting a spinning propeller into kidney artery through the guidewire. In certain embodiments, the method further comprises spinning the spinning propeller around the central guidewire and generate directional augmented renal artery blood flow toward the kidney.

In some embodiments provide a system comprising an invention device described herein for treating acute kidney injury. In certain embodiments, the acute kidney injury is contrast-induced acute kidney injury. In some embodiments, the device comprises a balloon catheter having a first balloon, a second balloon and at least one sensor associated with the second balloon. In certain embodiments, the device comprises two sensors described herein. In certain embodiments, the balloon catheter further comprises a side aperture for infusing normal saline or medication.

INCORPORATION BY REFERENCE

All publications, patents and patent applications mentioned in this specification are herein incorporated by reference to the same extent as if each individual publication, patent or patent application was specifically and individually indicated to be incorporated by reference.

BRIEF DESCRIPTION OF THE DRAWINGS

A better understanding of the features and advantages of the present invention will be obtained by reference to the following detailed description that sets forth illustrative embodiments, in which the principles of the invention are used, and the accompanying drawings of which:

FIG. 3A shows an cylinder-like inflated balloon. FIG. 3B shows the morphology of an exemplary inflated first balloon which is "butter-fly like. " FIG. 3C shows a cross-section view of the cylinder-like inflated balloon of FIG. 3A. FIG. 3D shows a cross-section view of the cylinder-like inflated balloon of FIG. 3B.

FIG. 16B shows the cross section top down view of FIG. 16A. FIGS. 16C and 16D show an umbrella-like device or a smaller second balloon as an anchor to facilitate the deployment of the tunnel membrane.

FIGS. 17A-17C shows another embodiment of invention disturbing means where a cone shaped wire device 1702 partially covered with tunnel membrane 1703 which is deployed from catheter 1701. FIG. 17A shows a side cross section view of an exemplary wire device 1702. FIG. 17B shows the specification of the exemplary wire device 1702 in aorta. FIG. 17C shows that a normal saline or other suitable medicine can be applied via an injection hole (or holes) 1708 via an infusion tube 1707 at the distal opening 1704 or the proximal opening 1705, or combination thereof.

FIGS. 18A-18D illustrate a variation of the embodiment of FIGS. 17A-17C where a cone-cylinder shaped wire device 1802 partially covered with tunnel membrane 1803 is shown. FIG. 18A show a side cross section view of the wire device 1802. FIG. 18B shows a top view of the wire device 1802. FIG. 18C shows a bottom view of the wire device 1802. FIG. 18D provide an isometric view of the wire device 1802.

DETAILED DESCRIPTION OF THE INVENTION

Current treatments/managements for acute kidney injury (AKI), especially contrast-induced acute kidney injury are mainly supportive. They include for example, (1) evaluating and stratifying patients with Mehran risk score before performing percutaneous coronary intervention (PCI), (2) avoiding high-osmolar contrast media by using low-osmolar or iso-osmolar contrast media, (3) reducing the amount of contrast media during PCI, and (4) applying intravenously isotonic sodium chloride solution or sodium bicarbonate solution hours before and after PCI, (5) avoiding use of nephrotoxic drugs (such as nonsteroidal anti-inflammatory drugs, aminoglycosides antibiotics, etc.) See Stevens 1999, Schweiger 2007, Solomon 2010. However, none of them were proven with consistent effect in preventing CI-AKI.

Provided herein are devices and systems that specifically focus on solving the two main pathophysiological culprits of CI-AKI, which are renal outer medulla ischemia and/or prolonged transit of contrast media inside the kidneys.

In some embodiments, there are provided a device for treating acute kidney injury (e.g., CI-AKI) comprising a balloon catheter having at least one balloon, at least one sensor associated with the balloon and a position indication means wherein the balloon occlude the orifice of both sides of renal arteries after inflation while allowing blood flow goes through the inflated balloon during application of the device inside abdominal aorta. In some embodiments, the position indication means is a radio-opaque marker, or the like.

Radio opaque marker is a vital prerequisite on an increasing number of endovascular medical devices. The value of radio opaque markers is clearly seen in visibility improvement during deployment of the device. Markers allow for improved tracking and positioning of an implantable device during a procedure using fluoroscopy or radiography.

In some embodiments, the device for treating CI-AKI comprising a balloon catheter having a first balloon, a second balloon, at least one sensor associated with the first balloon and a device position indication means wherein the first balloon occlude the orifice of both sides of renal arteries after inflation while allowing blood flow goes through the inflated balloon.

In some embodiments, there is provided a device for treating acute kidney injury, comprising: a balloon catheter having at least one balloon, at least one sensor associated with the balloon and a position indication means wherein the balloon occlude the orifice of both sides of renal arteries after inflation while allowing blood flow goes through the inflated balloon during application of the device inside abdominal aorta.

Figure 1:
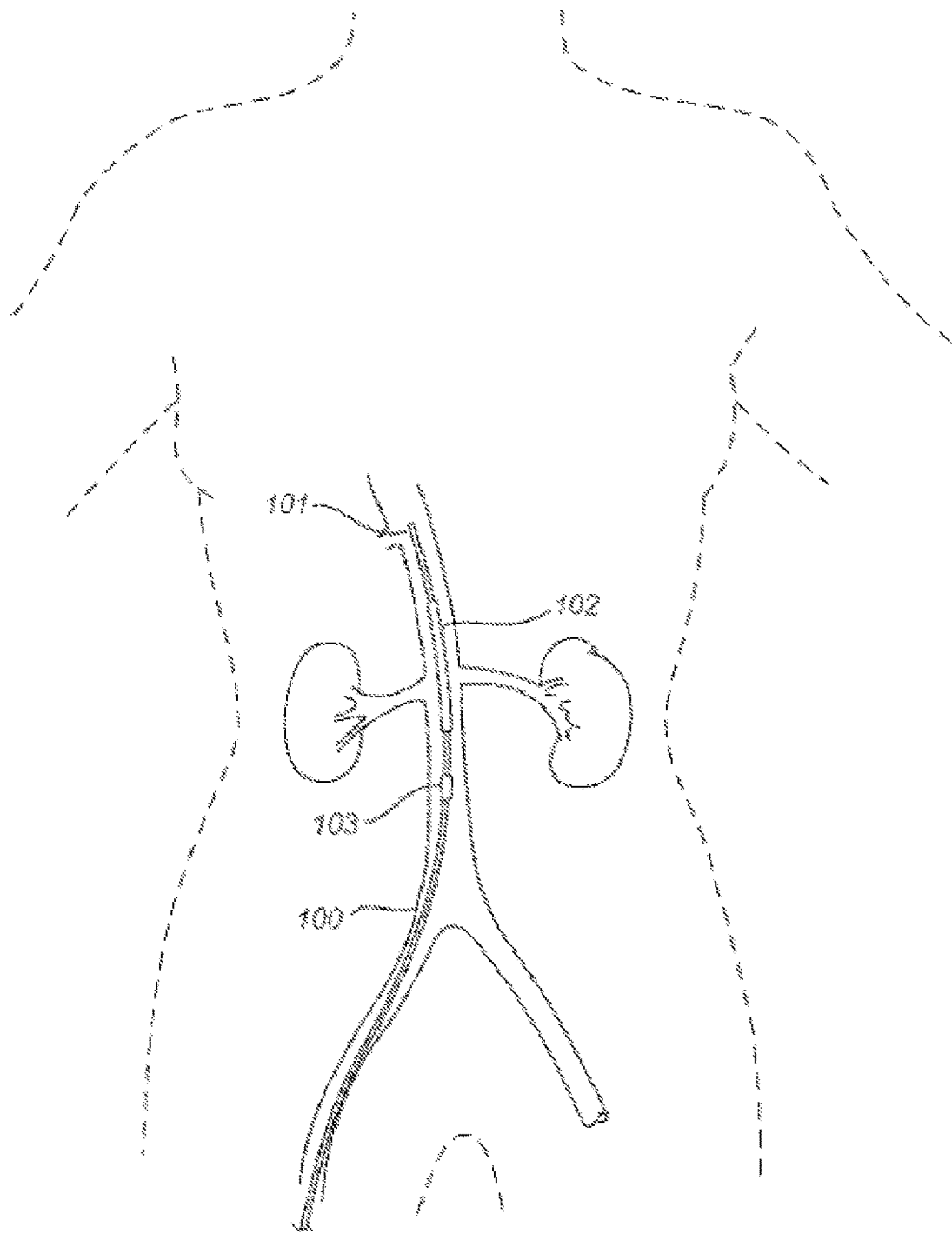
FIG. 1 illustrates a diagram of an exemplary invention device comprises a balloon catheter having a first balloon positioned at the supra-renal aorta position near orifices of bilateral renal arteries for treating acute kidney injury.

Referring to FIG. 1, an exemplary invention device 100 comprising a balloon catheter 101, a first balloon 102, a second balloon 103 and a radio opaque marker on the tip of the catheter 101 is shown. FIG. 1 shows that the device is inserted via femoral artery and the position of the device is monitored via a radio-opaque marker, or the like. The catheter of the device can be inserted into abdominal aorta by either transfemoral arterial approach or by trans-brachial artery approach or by trans-radial artery approach. The tip with radio-opaque marker is positioned to allow the first balloon at the supra-renal aorta position near orifices of bilateral renal arteries.

Figure 2:
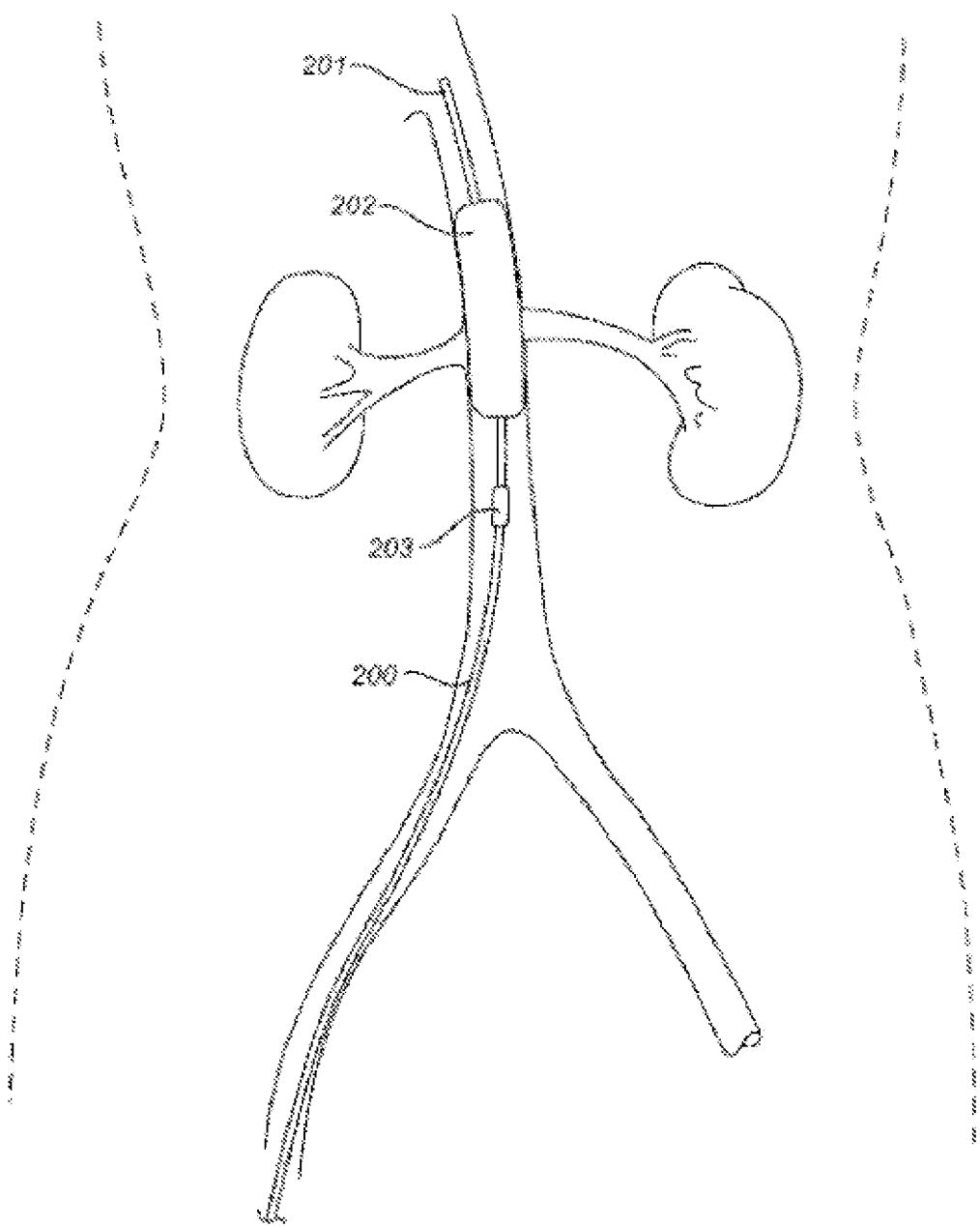
FIG. 2 illustrates a diagram of an exemplary invention device for treating acute kidney injury where first balloon is inflated to occlude the orifice of both sides of renal arteries.

Referring to FIG. 2, a diagram is shown that the device 200 comprising a catheter 201 having a first balloon 202 positioned at the supra-renal aorta position near orifices of bilateral renal arteries and the first balloon 202 is inflated where the inflated first balloon occlude the orifice of both sides of renal arteries so that the bolus influx of contrast media (or any other harmful agents during the application of the invention device) flowing from supra-renal aorta is prevented from entering into renal arteries and cause subsequent toxic effect. The second balloon 203 remains un-inflated.

In certain embodiments, the device comprises a balloon catheter having a first balloon, a second balloon and at least one sensor associated with the second balloon. In some embodiments, the device comprises a balloon catheter having a first balloon, a second balloon and at least one sensor associated with the second balloon.

Figure 3A:
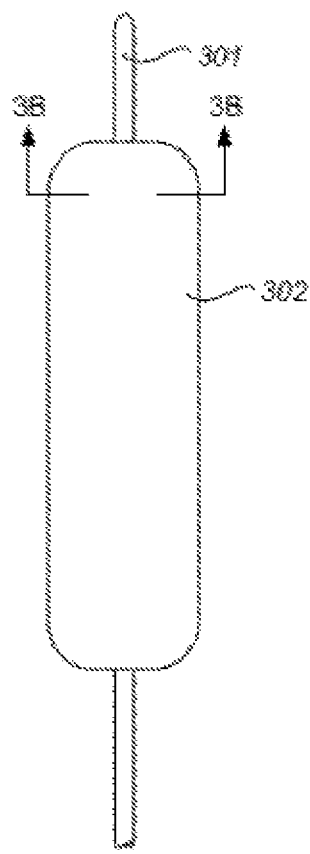
FIGS. 3A TO 3D are perspective views of first balloon of the invention device.
Figure 3B:
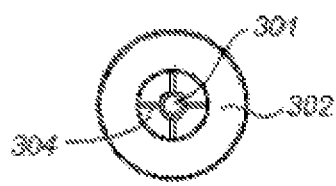
Figure 3C:
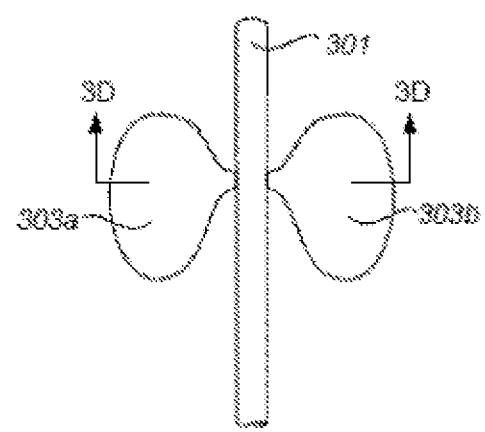
Figure 3D:
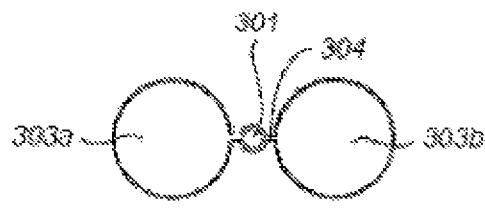

FIGS. 3A to 3D illustrate various embodiments of the first balloon. FIG. 3A shows an inflated first balloon 302 positions along with and circulates the catheter 301. The cross-section view of the inflatable first balloon of FIG. 3A shows a hollow area inside the balloon and outside the catheter 301 (a donut like balloon) allowing blood to flow along the catheter (FIG. 3B). The first balloon 302 is inflated via at least one connection tube 304 from the catheter 301 (four tubes shown in FIG. 3B). FIG. 3C shows other variation of the morphology of inflatable first balloon. A bilateral inflated balloon (303a and 303b) connected to each side of catheter 301 via connection tube 304 to occlude the orifices of both sides of renal arteries are shown in FIG. 3C, which also allows blood to flow along the catheter. FIG. 3D shows the cross-section view of the inflated first balloon of FIG. 3C (a butterfly like balloon). The butterfly like first balloon(s) are connected to the catheter via one or more connection tube 304 (shown one connection tube on each side of the catheter 301). In certain embodiments, the balloon has one, two, three, four or five connection tubes 304 for connection of the first balloon to the catheter and for inflation/deflation means.

In some embodiments, the first balloon is donut-like after inflation. In certain embodiment the first balloon is butterfly-like after inflation.

Figure 4:
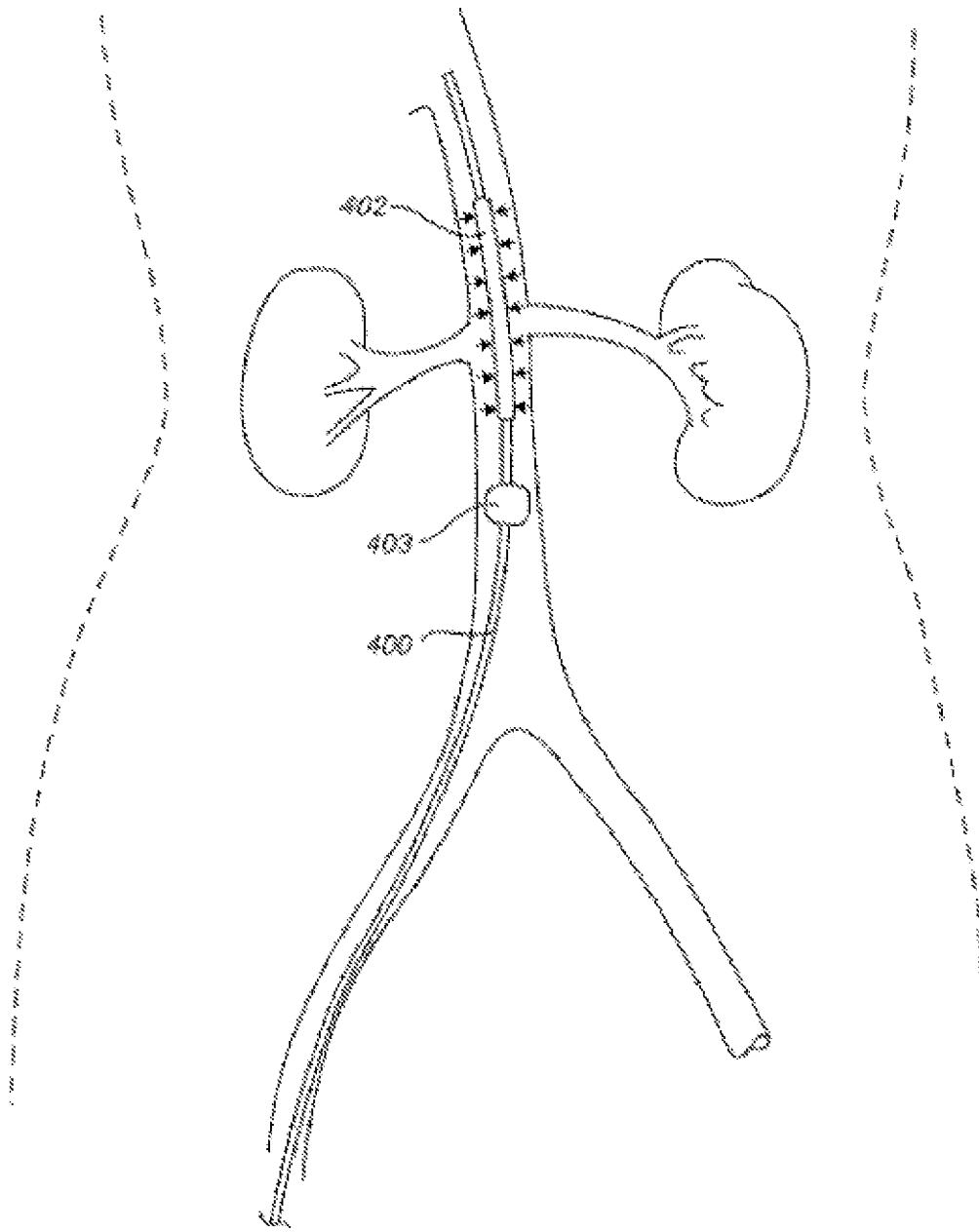
FIG. 4 illustrates a diagram showing deflated first balloon 402 and a second balloon 403 is inflated at the location of infra-renal aorta near the office of renal arteries.

Referring to FIG. 4, it is shown an exemplary device 400 comprising a deflated first balloon 402 after contrast media containing blood passed by and then the second balloon 403 is inflated at the location of infra-renal aorta near the orifice of renal arteries.

Figure 5:
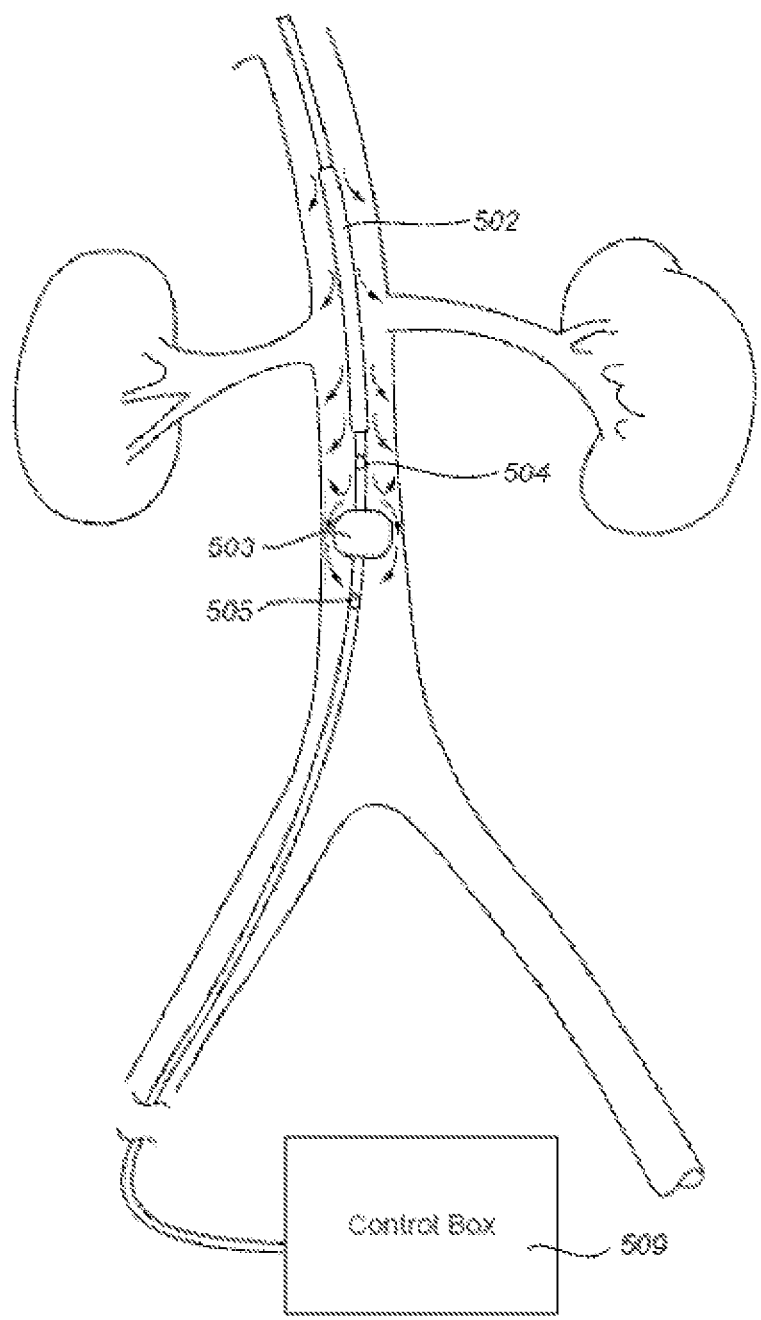
FIG. 5 illustrates a diagram showing the vortex blood flow caused by $2^{nd}$ balloon distension.

The inflation of the second balloon 503 is to the extent not totally occludes the aorta blood flow. As shown in FIG. 5, in the aorta, the vortex blood flow caused by the inflated second balloon distension will facilitate (augment) renal artery blood flow. In some embodiments, there is at least one sensor associated with the first balloon or second balloon for the control of inflation/deflation of either the first and/or second balloon. In some embodiments, the sensor is a pressure sensor. In some embodiments, the sensor is a size measuring sensor related to the size of either the first balloon or the second balloon. As shown in FIG. 5 as a non-limited example, there are one pressure sensor 504 at lower side of the first balloon (or at the upper side of the second balloon) and another pressure sensor 505 at lower side of the second balloon.

The analysis of data from the pressure sensors can be used as instantaneous titration of distention degree of the second balloon to provide adequate pressure gradient, and hence adequate vortex flow into renal arteries. In addition, the altered aorta blood flow will increase the renal artery blood flow, due to the location proximity and the diameter of the distended the second balloon. In some embodiments, the diameter of the distended second balloon is adjustable such that the diameter of the distended balloon is not too large to totally obstruct aorta blood flow and the altered aorta blood flow will not cause inadequacy of aorta blood flow at distal aorta or branches of aorta, i.e. right and left common iliac artery. Furthermore, the aorta wall will not be injured by the balloon distension.

Also shown in FIG. 5, there is a control box 509 outside the patient body, in connection with the balloon catheter. The control box will serve several functions: inflation and deflation of the first and second balloons, pressure sensing and/or measurement of upper and lower pressure sensors, normal saline titration via an included infusion pump with titratable infusion rate.

In some embodiments, there are two sets of pressure sensors, one at the supra-renal aorta side of the balloon, the other at the infra-renal aorta side of the balloon. The two sensors can continuously measure the pressure and the measured data can be exhibited at the control box outside of the patient's body. The pressure difference between the two sensors will be exhibited on the control box. Physicians can read the pressure difference and adjust the size of balloon by way of control box. Or the control box can do the adjustment of size of balloon automatically.

In some embodiments, the device for treating acute kidney injury further comprises a side aperture on the balloon catheter for application of normal saline or other medication infused from the control box, through the catheter into the supra-renal aorta. In some embodiments, normal saline (or other medication) is applied via a side aperture between the first and second balloon. In some embodiments, normal saline (or other medication) is applied via the tip of catheter.

Figure 6:
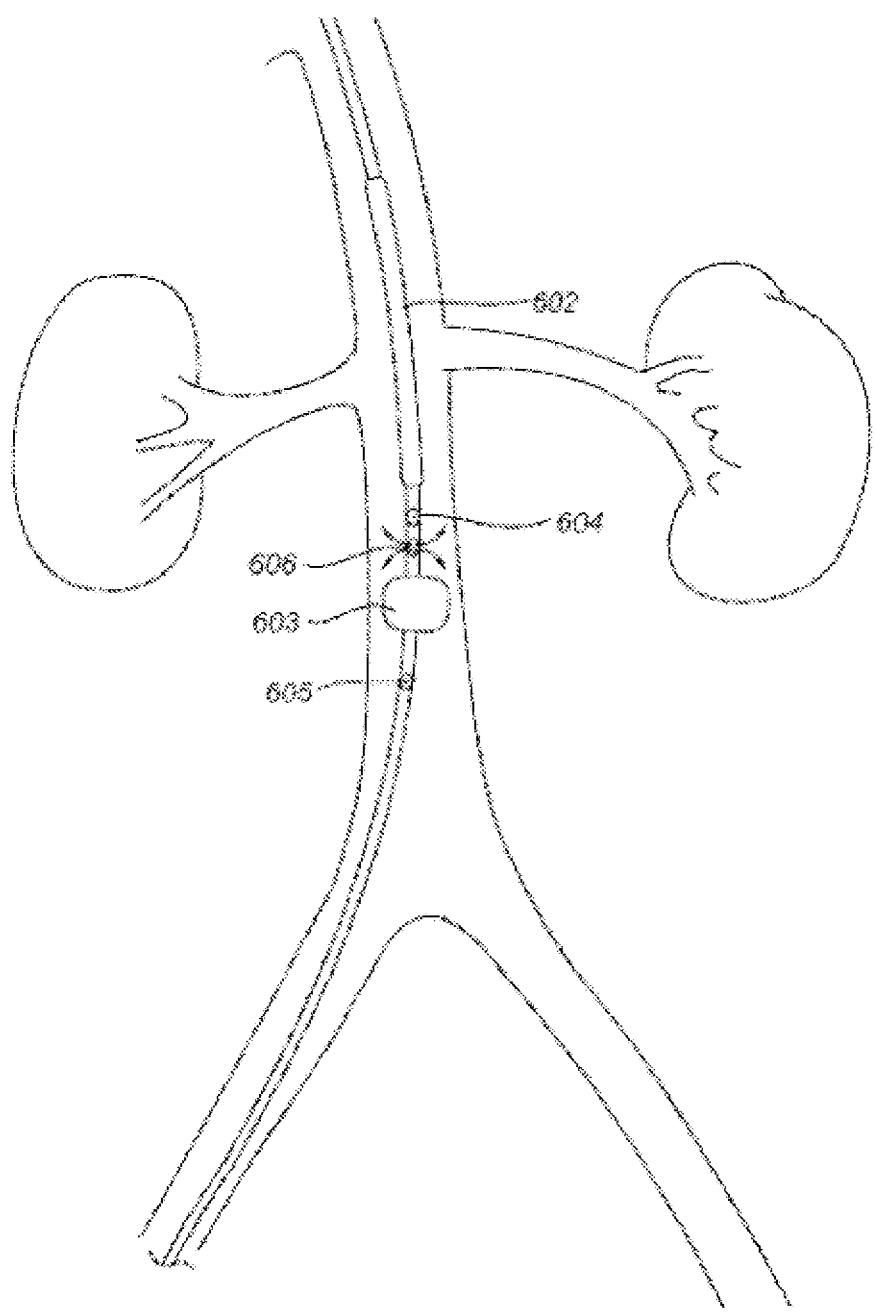
FIG. 6 shows that a normal saline can be infused from control box, through the catheter pore 606 into the supra-renal aorta while a second balloon remain inflated.

As illustrated in FIG. 6, an exemplary device for treating AKI comprising a first balloon 602, a second balloon 603 (shown inflated), a first sensor 604, a second sensor 605 and a side aperture 606 where normal saline can be infused into the supra-renal aorta via the side aperture 606. By infusion of normal saline into the supra-renal aorta, the renal artery blood flow can be further augmented. Furthermore, it avoids the direct fluid overload burden onto the heart, especially when patients already have congestive heart failure. For the treatment of CI-AKI, the infusion of normal saline into the supra-renal aorta also dilutes the concentration of contrast media in the supra-renal aorta, therefore reduces the concentration of contrast media and thus reduce the adverse effect of hyperviscosity caused by contrast media to the kidneys, after the contrast media flowing into the kidneys. In some embodiments, the infusion rate of normal saline through the side aperture into aorta can be controlled by the control box. In some embodiments, there is a control pump inside the control box to apply normal saline via the side aperture. In some embodiments, the control pump is in a separate unit. In some embodiments, the medication is a vasodilatory agent. In certain embodiments, the vasodilatory agent is Fenoldopam, or the like. In certain embodiments, the medication such as Fenoldopam, or the like is infused via the side aperture for prevention and/or treatment of CI-AKI.

Figure 7:
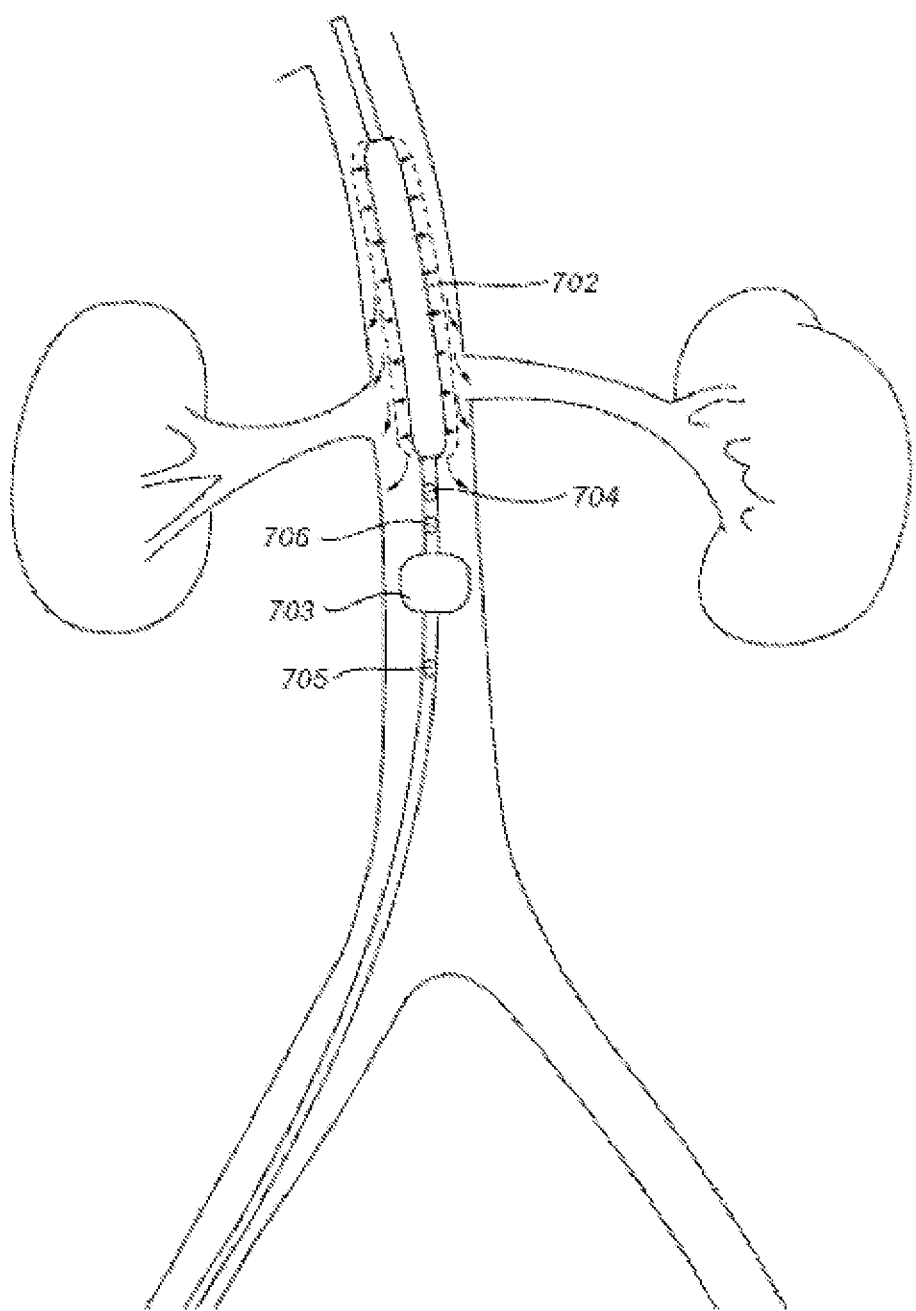
FIG. 7 shows another aspect of the invention where the first balloon exerts renal artery blood flow augmentation by periodic inflation and deflation of the first balloon.

FIG. 7 demonstrates another variation of the invention device comprising a balloon catheter having a first balloon 702, a second balloon 703 (shown inflated), at least one sensor (shown two sensors 704 and 705) and a side aperture where the first balloon 702 can exert renal artery blood flow augmentation by periodic inflation and deflation. As shown in FIG. 7, when the first balloon is inflated, it will not be inflated to totally occlude the orifice of renal arteries as shown in FIG. 2. Such periodic balloon inflation/deflation will cause blood flow into renal arteries.

Figure 8:
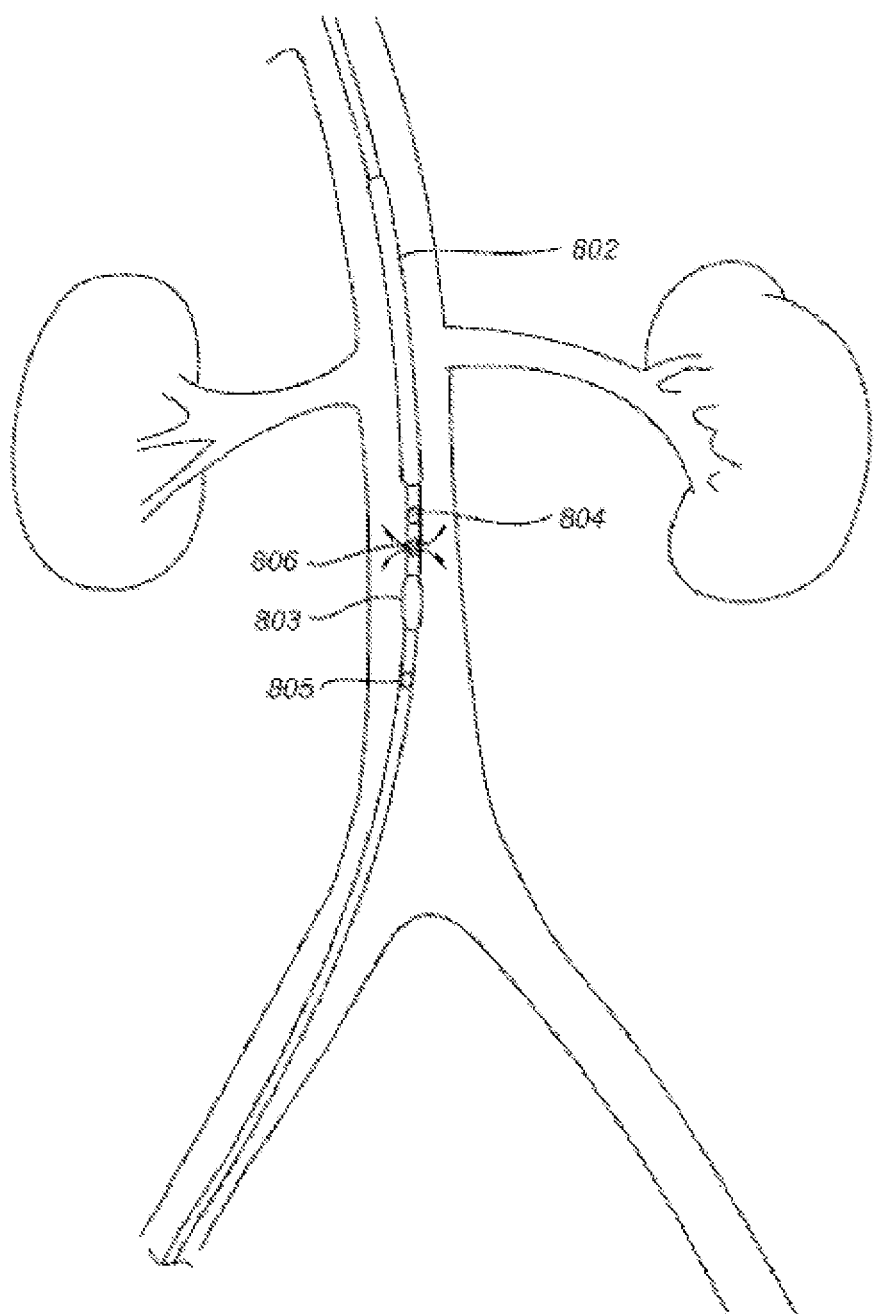
FIG. 8 shows at the end of PCI, both first and second balloon are deflated and normal saline as postprocedural hydration continuous infusion of normal saline as postprocedural hydration.

Referring to FIG. 8 at the end of percutaneous coronary intervention (PCI), both the first and second balloons will be deflated and either removed or remained inside aorta and normal saline will be continuously infused via a side aperture 806 as postprocedural hydration.

Figure 9:
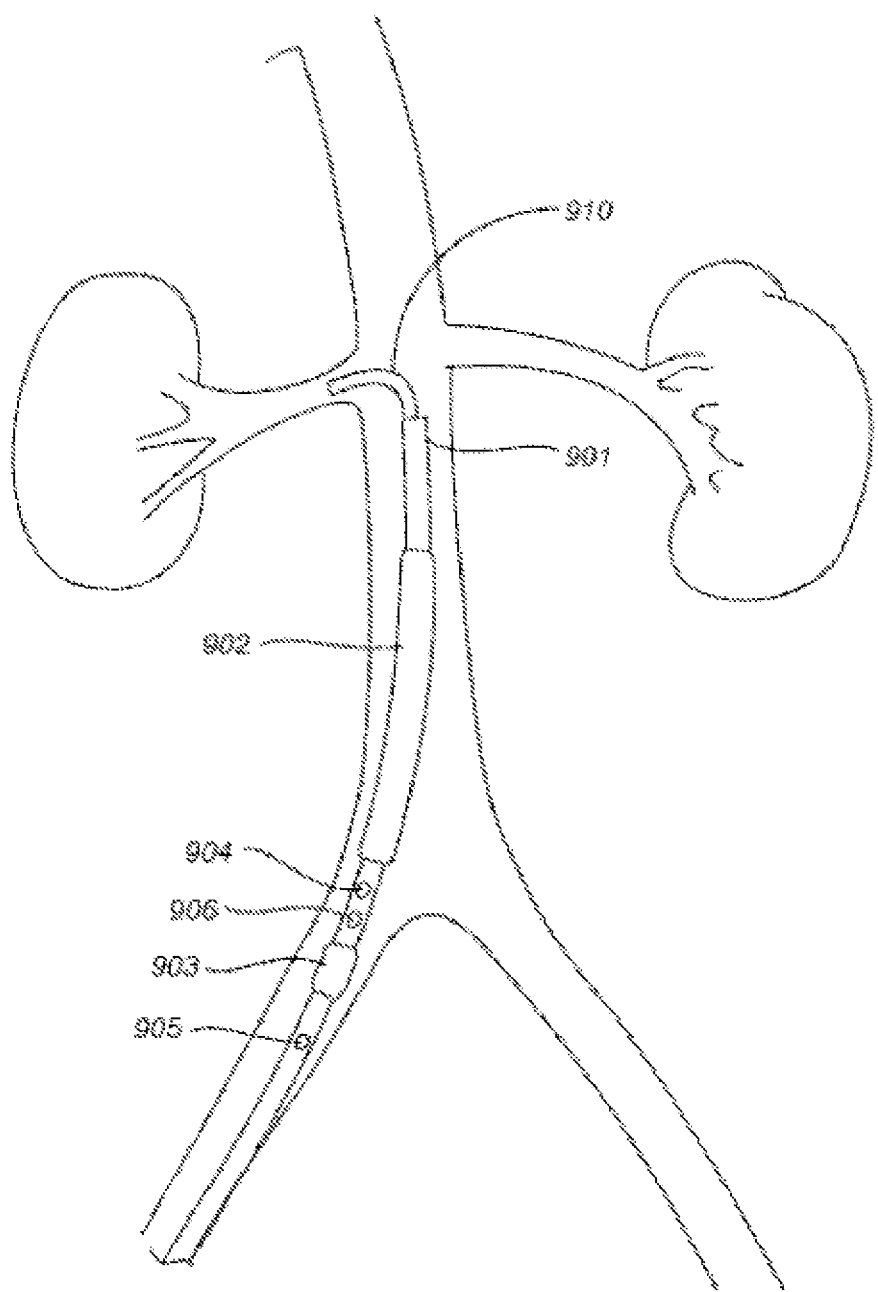
FIG. 9 shows another aspect of the present invention, where a guidewire is used to guide the device for insertion of renal artery.

As illustrated in FIG. 9, an exemplary device for treating AKI comprising a catheter 901, a first balloon 902, a second balloon 903, a first sensor 904, a second sensor 905, a side aperture 906 further includes a guidewire 910. The guidewire is inserted into renal artery via a catheter. When guidewire is inside renal artery, the outer sheath catheter is also inserted into renal artery.

Figure 10:
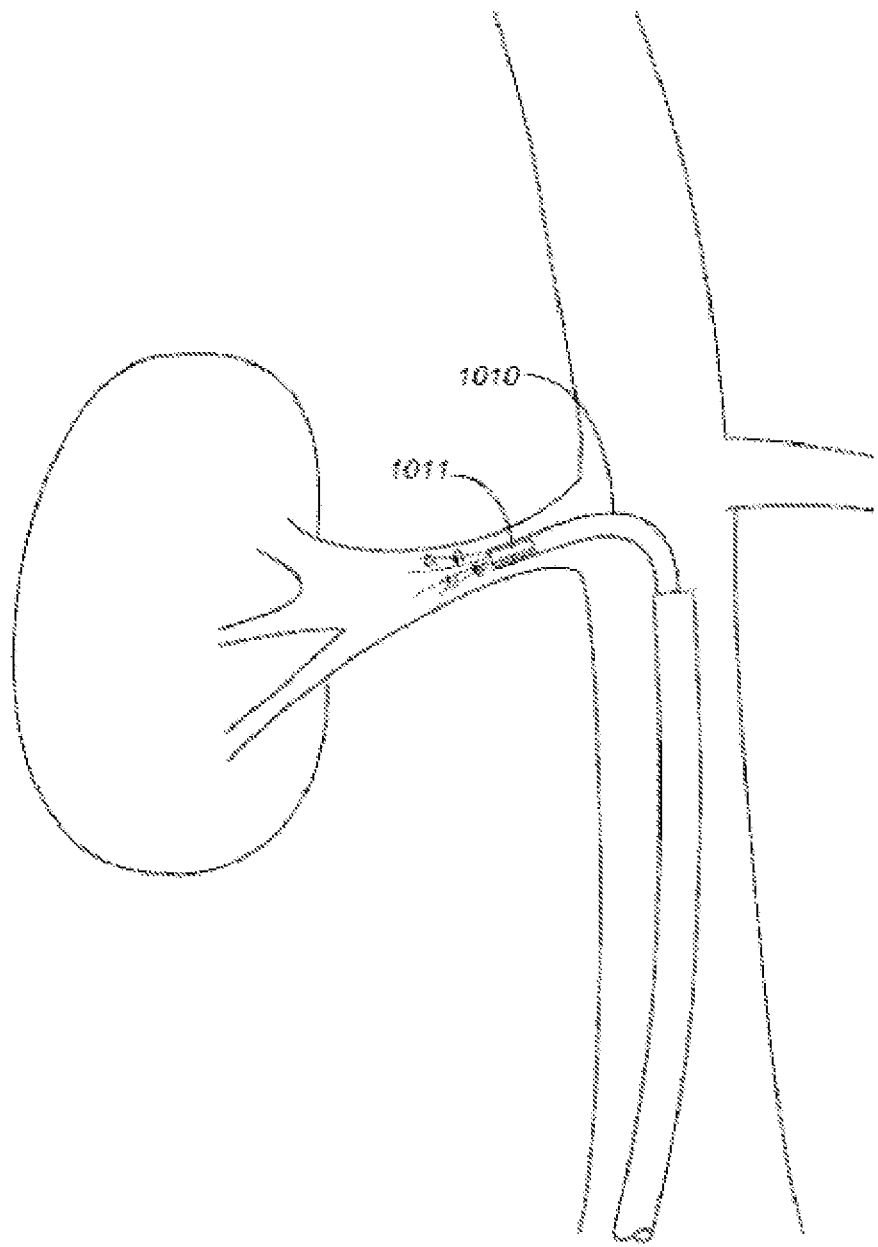
FIG. 10 shows that a spinning propeller is inserted to renal artery and then spins around the central guide wire to augment renal artery blood flow toward the kidney.

FIG. 10 shows that a spinning propeller 1011 is inserted from outer sheath catheter into renal artery through the guidewire 1010. The exemplary unidirectional flow pump such as a spinning propeller then spins around the central guidewire and generate directional augmented renal artery blood flow toward the kidney, hence achieves the goal of augmented renal artery flow.

Figure 11A:
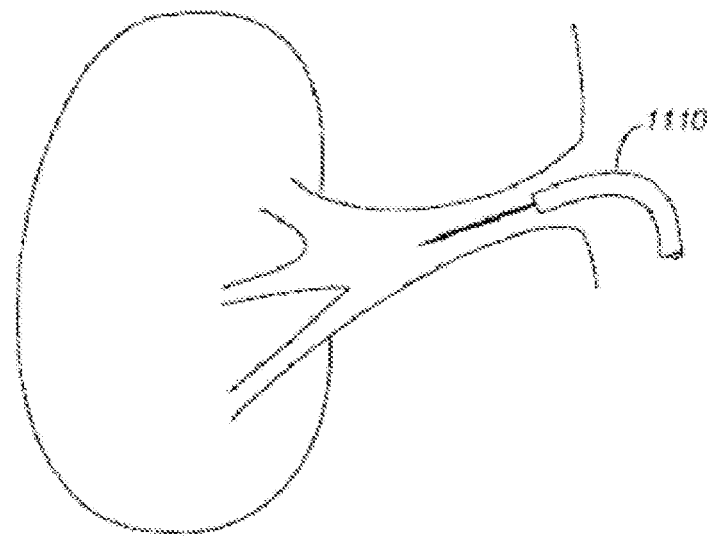
FIGS. 11A-11B show variation embodiments of a spinning propeller.
Figure 11B:
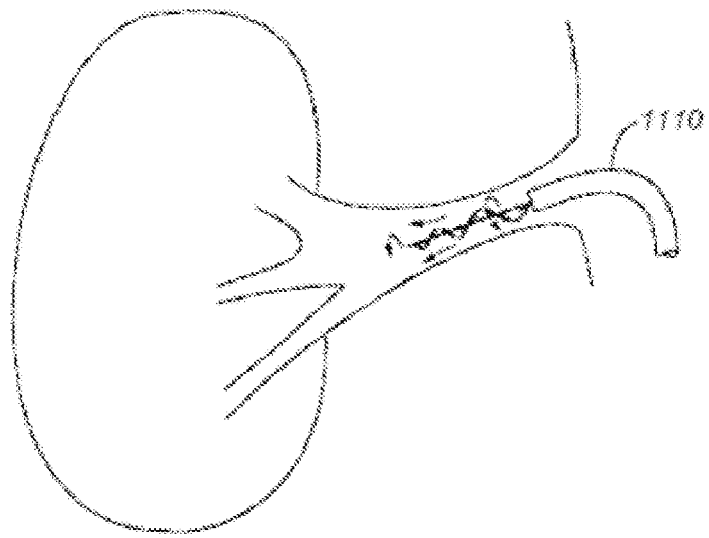

FIGS. 11A and 11B show variations of the spinning propeller. The spinning propeller in some embodiments is wing shape, fin shape, or the like.

In some embodiments, the balloon catheter further includes a guidewire and a spinning propeller. In certain embodiments, the spinning propeller spins around the central guidewire to generate directional augmented renal artery blood flow toward the kidney. In certain embodiments, the spinning propeller is wing shape or fin shape. In certain embodiments, the device further comprises another catheter comprising a guidewire and a spinning propeller to generate directional augmented blood flow to the other kidney. In certain embodiments, the additional catheter having a spinning propeller is functioned independently and simultaneously with the balloon catheter to generate directional augmented blood flow to each side of kidney.

MEMsPump

Microelectromechanical systems (MEMS) (also written as micro-electro-mechanical, MicroElectroMechanical or microelectronic and microelectromechanical systems and the related micromechatronics) is the technology of very small devices. MEMS are made up of components between 1 to 100 micrometers in size (i.e. 0.001 to 0.1 mm), and MEMS devices generally range in size from 20 micrometers (20 millionths of a meter) to a millimeter (i.e. 0.02 to 1.0 mm). They usually consist of a central unit that processes data (the microprocessor) and several components that interact with the surroundings such as microsensors. The fabrication of MEMS evolved from the process technology in semiconductor device fabrication, i.e. the basic techniques are deposition of material layers, patterning by photolithography and etching to produce the required shapes. Patterning in MEMS is the transfer of a pattern into a material. Typically, the most common MEMS pump have a patterned vibrating chamber connected a flow inlet and an outlet. This chamber is usually driven by piezoelectricity, such as the product of Bartels (http://www.micro-components.com). The vibration can also be driven by pneumatics (see e.g., Chun-Wei Huang, Song-Bin Huang, and Gwo-Bin Lee, "Pneumatic micropumps with serially connected actuation chambers," Journal of Micromechanics and Microengineering, 16(11), 2265, 2006), electrostatics (e.g., Tarik Bourouina, Alain Bossebuf, and Jean-Paul Granschamp, "Design and simulation of an electrostatic micropump for drug-delivery applications," Journal of Micromechanics and Microengineering, 7(3), 186, 1997), or electrothermal mechanism (Rumi Zhang, Graham A. Jullien, and Colin Dalton, "Study on an alternating current electrothermal micropump for microneedle-based fluid delivery systems," Journal of Applied Physics, 114, 024701, 2013).

Acoustic Wave Pump

Acoustic Streaming is ideal for microfluidic systems because it arises from viscous forces which are the dominant forces in low Reynolds flows and which usually hamper microfluidic systems. Also, streaming force scales favorably as the size of the channel, conveying a fluid through which an acoustic wave propagates, decreases. Because of acoustic attenuation via viscous losses, a gradient in the Reynolds stresses is manifest as a body force that drives acoustic streaming as well as streaming from Lagrangian components of the flow. For more information on the basic theory of acoustic streaming please see Engineering_Acoustics/Acoustic streaming. When applied to microchannels, the principles of acoustic streaming typical include bulk viscous effects (dominant far from the boundary layer, though driven by boundary layer streaming), as well as streaming inside the boundary layer. In a micromachined channel, the dimensions of the channels are on the order of boundary layer thickness, so both the inner and outer boundary layer streaming need to be evaluated to have a precise prediction for flow rates in acoustic streaming micropumps The derivation that follows is for a circular channel of constant cross section assuming that the incident acoustic wave is planar and bound within the channel filled with a viscous fluid. The acoustic wave has a known amplitude and fills the entire cross-section and there is no reflections of the acoustic wave. The walls of the channel are also assumed to be rigid. This is important, because rigid boundary interaction results in boundary layer streaming that dominates the flow profile for channels on the order of or smaller than the boundary layer associated with viscous flow in a pipe. This derivation follows from the streaming equations developed by Nyborg who starts with the compressible continuity equation for a Newtonian fluid and the Navier-Stokes and dynamic equations to get an expression for the net force per unit volume. Eckart uses the method of successive approximations with the pressure, velocity, and density expressed as the sum of first and second order terms. Since the first order terms account for the oscillating portion of the variables, the time average is zero. The second order terms arise from streaming and are time independent contributions to velocity, density, and pressure. These non-linear effects due to viscous attenuation of the acoustic radiation in the fluid are responsible for a constant streaming velocity.

Acoustic wave devices such as surface acoustic wave (SAW) devices have been in commercial use for more than 60 years, with their main applications in communications (e.g., filters and oscillators in mobile phone or televisions). Various microfluidic acoustic wave pumps have been developed to control, manipulate, and mix the minute amount of liquid in microliter to picoliter volumes, including devices based on mechanical moving parts (such as oscillating membranes), electric fields applied to liquids, magnetic fields applied to fluids or inducing phase changes in fluids. The surface acoustic wave in some instances is generated by applying a rf signal to a set of interdigitated transducers (IDTs) which lie on top of a piezoelectric material. When the frequency, f, of the rf signal is equal to Vs/p, where Vs is the acoustic velocity of the substrate/piezoelectric system and p is the periodic spacing of the IDT electrodes, then constructive interference occurs and an intense acoustic wave is generated which travels through the piezoelectric substrate. The mode of the acoustic wave is determined by the crystallographic orientation of the piezoelectric material and, in the case of devices using a thin film piezoelectric, the thickness of the piezoelectric layer. For microfluidic applications, a component of the acoustic wave is required in the direction of propagation, and the so -called Rayleigh mode is commonly employed in which an individual atom performs elliptical motion in the plane perpendicular to the surface and parallel to the direction of propagation. However, the excessive damping of the Rayleigh mode by the liquid means that this mode is considered to be unsuitable for sensing applications. The coupling of the acoustic wave into liquid on the surface of the SAW device, which is required for pumping or mixing, occurs through the excited longitudinal waves propagating into the liquid at an angle called the Rayleigh angle, following the Snell law of diffraction as below: The Rayleigh angle, theta, is defined by $$v = \sin^{-1}\left(\frac{V_L}{V_S}\right)$$

where $V_L$ is the velocity of the longitudinal wave in the liquid. However, the energy and the momentum of the longitudinal wave radiated into the liquid are quite useful for liquid pumping and mixing (X. Du et al, "ZnO film based surface acoustic wave micro-pump," Journal of Physics: Conference Series, 76(1), 012047, 2007). A skilled person in the art could prepare and employ an acoustic wave pump based on the theory provided above.

Figure 12:
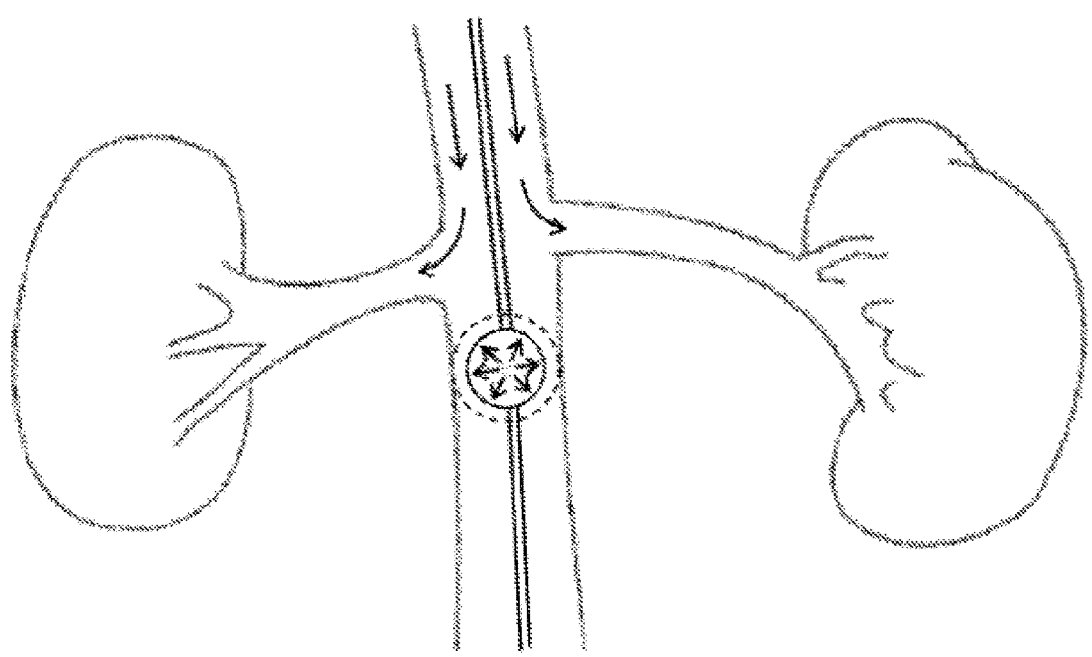
FIG. 12 illustrates an exemplary balloon type acoustic wave pump at work.
Figure 13A:
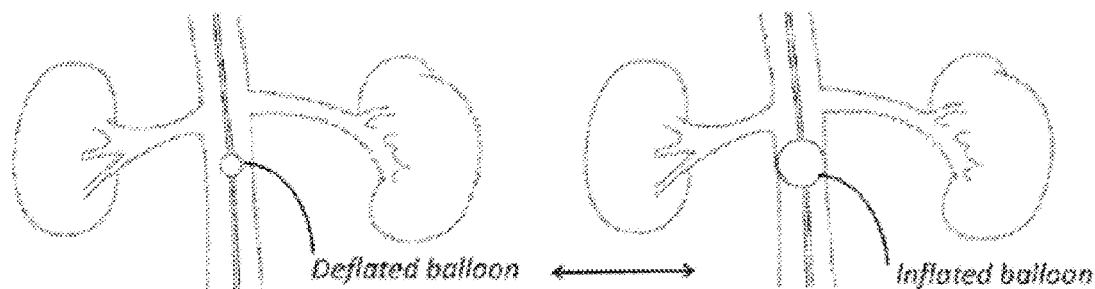
FIGS. 13A-13B provides how the exemplary acoustic wave pump works via the inflation and deflation of the balloon.
Figure 13B:
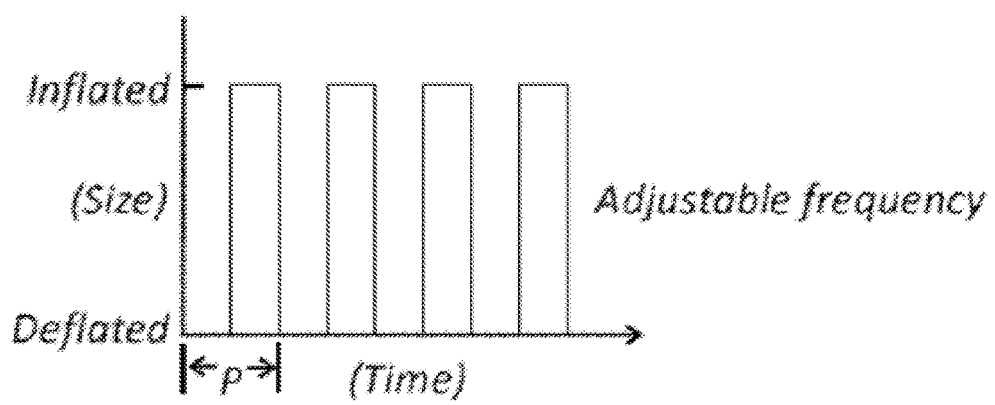
Figure 14A:
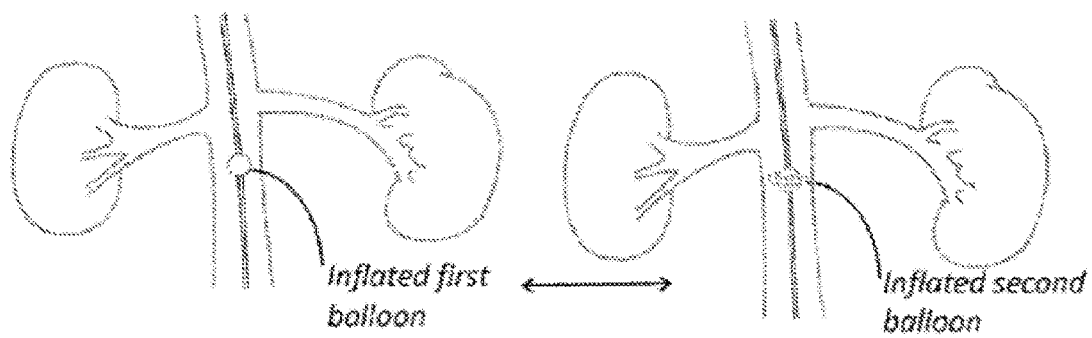
FIGS. 14A-14B illustrate yet another embodiment where two balloons are involved to create acoustic wave where the first balloon is inflated at a pre-determined size allowing the second balloon around the first one to create acoustic wave.
Figure 14B:
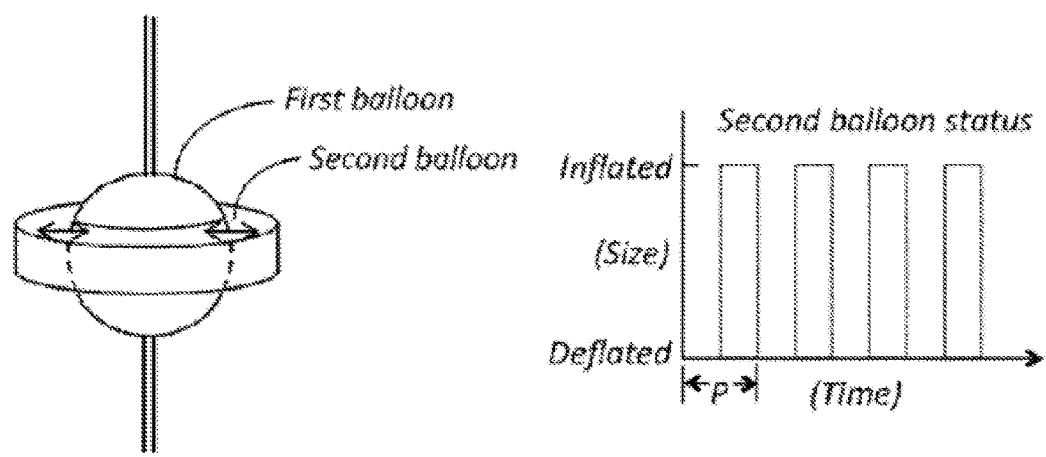

As illustrated in FIG. 12, an exemplary acoustic wave pump is employed near renal arteries. The exemplary acoustic wave pump include an inflatable first balloon where at its deflated stage, the blood stream can flow through freely. The first balloon then inflates and deflates in a preset adjustable frequency to create acoustic wave which forces the blood flow to enter renal arteries (see FIGS. 13A-13B). In some embodiments, the balloon is fully inflated where its outer circumference contacts the aorta wall which defines as 100% inflation. In some embodiments, the balloon is inflated 90%, 80%, 70%, 60%, 50%, 40%, 30%. In some embodiments, the balloon is inflated 99.9% to 10%, 80% to 20%, 70% to 30%. In some embodiments, the shape of the balloon varies from sphere, cylinder, donut-like to sausage-like shape. The inflation-depletion period (P) is adjustable. FIGS. 14A-14B illustrate yet another embodiment where two balloons are involved to create acoustic wave. FIG. 14A shows a second balloon inflated and deflated around a first balloon that is inflated to a pre-determined size. The inflated first balloon induces a consistent pressure increase in aorta to facilitate blood flowing into renal arteries. The wave frequency can be adjusted so the donut-like second balloon can create desire blood flow toward renal arteries. The first and second balloons are fully inflated in each own inflation state. The full inflation is to prevent unexpected balloon deformation due to aorta blood flow. In certain embodiments, the first balloon and the disturbing means is coated with contrast-media absorber to remove contrast media from the blood so that it can dilute the contrast media concentration, further reducing the harm by contrast media to kidneys.

In some embodiments, the balloon catheter further includes a guidewire and a flow augmentation means to generate directional augmented renal artery blood flow toward the kidney. For example, the flow augmentation means comprise a spinning propeller, a micro-electro-mechanical (MEM) micropump, an acoustic wave pump, or the like. In some embodiments, the flow augmentation means is a spinner propeller. In some embodiments, the flow augmentation means is a micro-electro-mechanical (MEM) micropump. In some embodiments, the flow augmentation means is an acoustic wave pump.

Figures 15A, 15B:
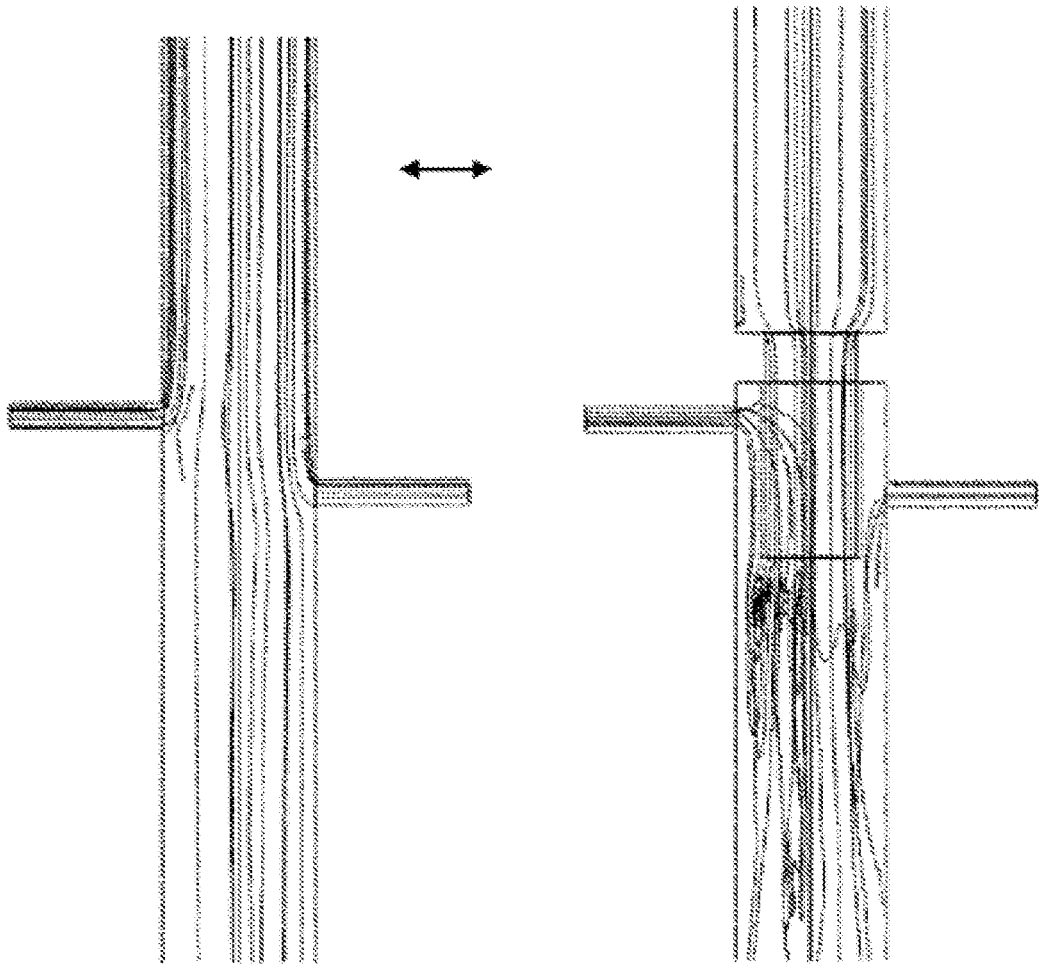
FIGS. 15A-15B show computer generated blood flow simulation diagrams without (FIG. 15A) and with (FIG. 15B) a first balloon attached with a tunnel membrane. The curved lines represent the streamlines.

Referring to FIGS. 15A and 15B, the computer generated blood flow simulation diagrams without (15A) and with (15B) a first balloon (e.g., a donut-like balloon after inflation) attached with a tunnel membrane are shown. The curved lines represent the streamlines. Upon inflation, the first balloon is inflated to form a hollow cylinder. The outer wall of the inflated balloon is in contact with the aorta wall. The inflated balloon exerts its function by the following mechanism. The stagnation region, where the blood flow rate is zero, is formed adjacent to the upper wall of the inflated balloon as the blood flow is in laminar regime. As the blood flows through the balloon hole, a new boundary layer along the sidewall of the balloon hole is generated so that the blood flow is focused at the very central part of aorta. As a result, the blood flow in periphery part of aorta will be detoured to more central part of aorta so that the bolus influx of contrast media flowing from supra-renal aorta can be retarded into renal artery orifice. Hence the subsequent toxic effect by contrast medium to kidneys can be reduced. The flow field in aorta without and with the invention can be compared in FIGS. 15A and 15B, respectively.

The streamlines, represented by the curved lines in FIGS. 15A and 15B, indicate the routes of sampling blood mass flow from the supra-renal aorta. Comparing to FIG. 15A, the simulation diagram in FIG. 15B shows that the streamlines curved toward the central part of the aorta right before the blood flow passes through the first balloon, which proves that the first balloon indeed cause the blood flow to the very central part of aorta. As shown in FIG. 15A, without the first balloon, the streamlines go from the supra-renal aorta into the renal arteries directly, indicating that the renal arteries intake blood flow directly from the supra-renal aorta where the concentration of contrast media is high. With the first balloon in position (see FIG. 15B) some streamlines go from supra-renal aorta toward infra-renal aorta before entering renal arteries, indicating that the renal arteries intake blood flow from the infra-renal aorta, where the contrast media has been diluted by the blood flow.

These results (flow field in aorta with or without the first balloon) provide guidance to design yet another embodiment where a flow disturbing means is associated with the balloon. In some embodiments, the flow disturbing means is a tunnel membrane attached to the first balloon adapted to fit inside an aorta wall. In some embodiments, the flow disturbing means is an umbrella-like blood flow reducing component either attached to the catheter or to the first balloon positioned above or below renal arteries (suprarenal or infrarenal aorta areas). In some embodiments, the flow disturbing means is an umbrella-like blood flow reducing component attached to the catheter positioned at suprarenal aorta. A skilled person in the art would readily recognize any similar shapes, structures, or functions as to an umbrella-like blood flow reducing component. Without the flow disturbing means, the renal arteries intake blood directly from the supra-renal aorta where high concentration of contrast media is contained, as shown in FIG. 15A. When the disturbing means (with or without the first balloon) is applied (as shown in FIG. 15B), the renal arteries intake blood from the infra-renal aorta where the concentration of contrast media reduced. The curved lines inside the tube in FIGS. 15A and 15B represent the streamlines of blood flow. In FIG. 15B, contrast media goes to the infra-renal aorta with the disturbed blood flow and is hence diluted before in-taken into the renal arteries.

The flow disturbing means is any device that can disturb blood flow resulting to a lesser renal arteries blood intake from the infra-renal aorta. Based on the practice of the present invention, a skilled person in the art can readily apply any similar device of FIG. 16A, 16C, 16D, 17A, 17C, or the like.

Figure 16A:
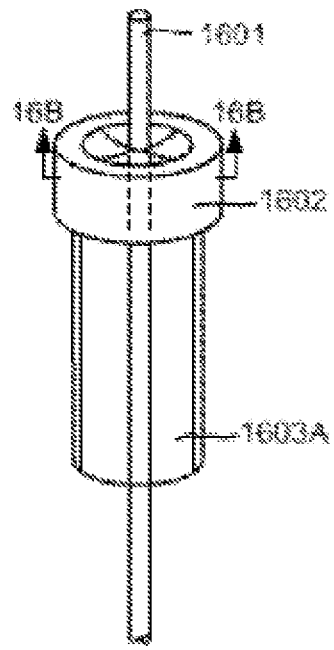
FIGS. 16A-16D show another aspect of the present invention where a disturbing means such as a tunnel membrane 1603A (extension from the inner rim of the first balloon) is expended/extended toward the infra-renal aorta to further confining the renal arteries to intake blood flow from the infra-renal aorta.
Figure 16C:
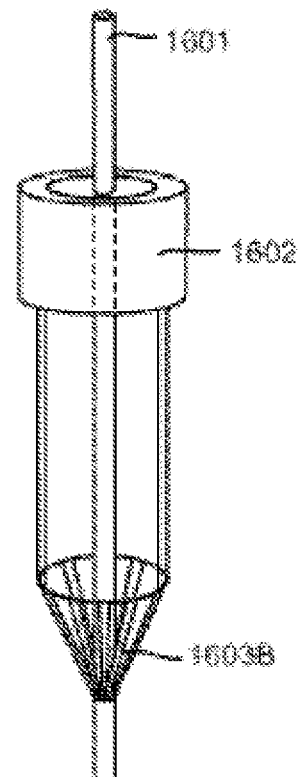
Figure 16B:
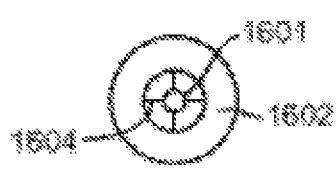
Figure 16D:
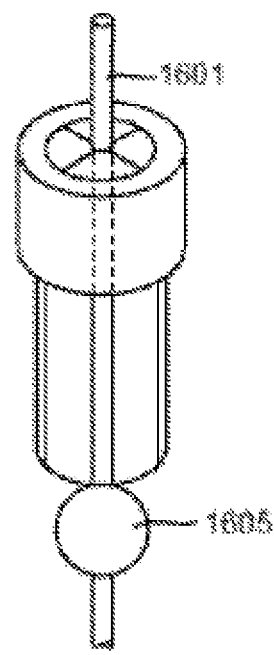

As illustrated in FIG. 16A, a first balloon 1602 with a disturbing means (e.g., a tunnel membrane 1603A) is shown. FIG. 16B is a cross section view from top of FIG. 16A where at least one connection tube 1604 from the catheter 1601 is shown. The cross sectional view of the $1^{st}$ balloon showed a halo area inside the balloon, so that the halo area can provide passage of aorta blood flow from supra-renal aorta to infra-renal aorta. One variation of the morphology of the first balloon with a disturbing means is to have a second balloon attached to the tunnel membrane (e.g., as shown in FIG. 16D). The first balloon expected to locate at supra-renal aorta is larger in diameter and it can be attached to the aorta wall, where as the other balloon is smaller in diameter providing drag to deploy the tunnel membrane. In some embodiments, the first balloon does not require to be attached to the aorta wall, leaving small space around the first balloon allowing blood seeping through. FIG. 16C yet illustrates another embodiment of the disturbing means where an umbrella-like blood flow reducing component 1603B is shown. While in the insertion mode, the umbrella-like blood flow reducing component 1603B is folded allowing free flow of blood stream. Once the device is at position where the disturbing means is near and below the renal arteries, the umbrella-like blood flow reducing component 1603B is unfolded due the downward blood flow direction. The component may be a second balloon 1605 attached to the tunnel membrane (see FIG. 16D). The disturbing means (e.g., a tunnel membrane, an umbrella-like blood flow reducing component, or the like) is made of material with flexibility. In some embodiments, they are made of soft plastics. In some embodiments, they are made of semi-soft plastics. In other embodiments, they are made of metal with the flexibility character such as metal wire. The tunnel membrane, in some embodiments, is a flexible film such as polytetrafluoroethene, expanded polytetrafluoroethene, silicone rubber, polyurethane, poly(ethylene terephthalate), polyethylene, polyether ether ketone (PEEK), polyether block amide (PEBA), or the like.

In some embodiments, the infra-renal side of the balloon or the disturbing means (such as infra-renal tunnel membrane) can inject saline via injection hole into the aorta to dilute the contrast media before it flows into the renal arteries. The injection holes, in some embodiments, are located at the first balloon. The injection holes, in some embodiments, are located at catheter near the first balloon. The injection holes may be part of the balloon or the catheter. In some embodiments, the injection holes are located at an infusion tube. The material of the such infusion tube, in some embodiments, is selected from the group consisting of teflon, polyoxymethylene copolymer, polyimides, polycarbonate, polyetherimide, polyetheretherketone, polyethylene, polylactic acid, polylactide acid, polystyrene, polyurethane, PVC, thermoplastic elastomer, and combinations thereof, and the like.

As illustrated in FIG. 17A, which provides yet another embodiment of the flow disturbing means, is a cone shaped wire device 1702 partially covered with tunnel membrane 1703 which is deployed from catheter 1701. FIG. 17B provides an exemplary specification of the cone shaped wire device 1702 of FIG. 17A where the diameter of the distal opening 1704 is about 3 to 3.2 cm or about 3.0 cm. Thus the outer rim of the wire device 1702 is either tightly fitted inside the aorta (of e.g., 3.0 to 3.2 cm diameter) or loosely situated with little space allowing blood seeping through. The diameter of the distal opening 1704 is based on various diameters of an aorta (typically from about 5 cm to about 2 cm) in the patients where the device is deployed. In some embodiments, the distal opening has a diameter of about 5 cm to about 1.5 cm; in some embodiments, the distal opening has a diameter of about 4.5 cm to about 1.7 cm; in some embodiments, the distal opening has a diameter of about 4 cm to about 1.8 cm; about 3.5 cm to about 1.8 cm; or about 3 cm to about 2.0 cm. A tunnel membrane 1703 is covered from the edge of the distal opening 1704 to the proximal opening 1705 of the wire device. The height (1706, see FIG. 17B, where is the distance of blood flowing through) of the tunnel membrane in some embodiments is about 1.5 cm to about 4 cm, about 2 cm to about 3.5 cm, about 2.5 cm to about 3.0 cm (as shown in FIG. 11B is 3 cm). In some embodiments, the height 1706 of the tunnel membrane is about 2 cm, about 3 cm, or about 4 cm. The proximal opening 1705 allows the blood flow through with restricted speed that creates a disturbing of blood flow allowing that the renal arteries intakes blood flow from the infra-renal aorta, where the contrast media has been diluted by the blood flow. To create such an effective blood flow disturbing caused by a disturbing means (e.g, the device 1702), in some embodiments, the diameter of the proximal opening is about one-fourth to about three-fourth of the diameter of the distal opening. In some embodiments, the diameter of the proximal opening is about one-third of the diameter of the distal opening. For example, as shown in FIG. 17B the diameter of the bottom opening 1705 is about 1.0 cm. Relative to where the blood flowing through from the proximal opening, blood releasing height 1709 is designed to be about one-half to about three times of the diameter of the proximal opening. The ratio relationship between blood releasing height 1709 and proximal opening 1705 is based on (1) how the wire device restricts blood flow which creates disturbance, (2) the structural strength of the wire device, and (3) the diameter relationship between the distal opening and the proximal opening.

To support such cone shaped structure, the wire device comprises wires 1710 with at least 3 wires. In some embodiments, there are 4 to 24 wires, 5 to 22 wires, 6 to 20 wires, 8 to 18 wires, or 10 to 16 wires. In some embodiments, there are 3, 4, 5, 6, 7, 8, 9, 10, 11, 12, 13, 14, 15, 16, 17, 18, 19, or 20 wires in the wire device partially covered with tunnel membrane. If needed, a skilled person in the art can prepare a wire device in accordance with the practice of the present invention to any number of wires suitable to provide a disturbing means. The wire may be any superelastic material such as nitinol.

Pseudoelasticity, sometimes called superelasticity, is an elastic (reversible) response to an applied stress, caused by a phase transformation between the austenitic and martensitic phases of a crystal. It is exhibited in shape-memory alloys. Pseudoelasticity is from the reversible motion of domain boundaries during the phase transformation, rather than just bond stretching or the introduction of defects in the crystal lattice (thus it is not true superelasticity but rather pseudoelasticity). Even if the domain boundaries do become pinned, they may be reversed through heating. Thus, a superelastic material may return to its previous shape (hence, shape memory) after the removal of even relatively high applied strains.

The shape memory effect was first observed in AuCd in 1951 and since then it has been observed in numerous other alloy systems. However, only the NiTi alloys and some copper-based alloys have so far been used commercially.

For example, Copper-Zinc-Aluminum (CuZnAl) was the first copper based superelastic material to be commercially exploited and the alloys typically contain 15-30 wt % Zn and 3-7 wt % Al. The Copper-Aluminum, a binary alloy, has a very high transformation temperature and a third element nickel is usually added to produce Copper-Aluminum-Nickel (CuAlNi). Nickel-Titanium Alloys are commercially available as superelastic material such as nitinol. In some embodiments, the superelastic material comprises copper, aluminum, nickel or titanium. In certain embodiments, the superelastic material comprises nickel or titanium, or combination thereof. In certain embodiments, the superelastic material is nitinol.

Specific structures can be formed by routing wires (bending one or a few wires and weaving into final shape) or cutting superelastic tube (laser cutting out the unwanted parts and leaving final wires in place) or cutting superelastic fleet (laser cutting out the unwanted parts and annealing the fleet into a cone shape.

Similarly, in some embodiments, the disturbing means (e.g., the wire device 1702) can inject saline from one or more injection hole 1708 via an infusion tube 1707 at the distal opening 1704 or the proximal opening 1705, or combination thereof into the aorta to dilute the contrast media further before it flows into the renal arteries. See FIG. 17C. In some embodiments, the injection hole(s) is on the catheter, for example at the position close to the tip of the catheter where the disturbing means is deployed.

In some embodiments, the cone shaped wire device comprises an upper cylinder portion 1811 as illustrated in FIG. 18A. The upper cylinder portion 1811 is used to form tight contact of the device on the aorta wall. This tight contact supports the device against high pressure due to high blood flow rate. This tight contact prevents contrast media from leaking through the contact interface (without blood seeping through). To avoid occlusion of arteries branching from supra-renal aorta by upper cylinder portion, which is about 0.5 cm apart, the height of the upper cylinder portion should not be more than 0.5 cm to avoid blocking artery branches. The height 1806 of the distal opening to the proximal opening should be about 1.5 cm to about 4 cm, about 2 cm to about 3.5 cm, or about 2.5 cm to about 3.0 cm.

As illustrated in FIG. 18A (a side view), which provides yet a variation of the embodiment of FIGS. 17A-17C, a cone-cylinder shaped wire device 1802 partially covered with tunnel membrane 1803 from the rim of the distal opening 1804 to proximal opening of 1805, which is deployed from catheter 1801. FIG. 18B shows a top view of the wire device 1802. FIG. 18C shows a bottom view of the wire device 1802. FIG. 18D provide an isometric view of the wire device 1802.

In another aspect, a method for treating contrast-induced acute kidney injury is disclosed. The method comprises: inserting the catheter of claim 1 to abdominal aorta; placing the catheter at suprarenal aorta; and deploying the disturbing means at a position allowing the disturbing means to provide blood flow disturbance which makes a contrast media become diluted before taking into the renal arteries. In certain embodiments, the insertion of the device to abdominal aorta is applied either by transfemoral artery approach or by trans-branchial artery approach or by trans-radial artery approach. In some embodiments, the balloon catheter further includes a guidewire and a flow augmentation means. In some embodiments, the method further comprises infusing normal saline and/or suitable medication from one or more injection holes (via an infusion tube, or the catheter) into the supra-renal aorta.

In another aspect, a method for treating contrast-induced acute kidney injury is disclosed. The method comprises: inserting the invention device comprising a balloon catheter having a first balloon, a second balloon, at least one sensor to abdominal aorta; placing the balloon catheter at a position allowing the first balloon at the supra-renal aorta position near orifices of bilateral renal arteries; inflating the first balloon to occlude the orifice of both sides of renal arteries during the application of contrast media; deflating the first balloon after the contrast media has completely employed; inflating the second balloon to the extent not totally occlude the aorta blood flow at the location of infra-renal aorta near the orifice of renal arteries; deflating the second balloon; and infusing normal saline and/or suitable medication via the side aperture into the supra-renal aorta.

In some embodiments, the insertion of the device to abdominal aorta is applied either by transfemoral arterial approach or by trans-brachial artery approach or by trans-radial artery approach. In certain embodiments, the balloon catheter further includes a guidewire and a spinning propeller. In certain embodiments, the method further comprises inserting a guidewire into renal artery. In certain embodiments, the method further comprises inserting a spinning propeller into kidney artery through the guidewire. In certain embodiments, the method further comprises spinning the spinning propeller around the central guidewire and generate directional augmented renal artery blood flow toward the kidney.

In some embodiments provide a system comprising an invention device described herein for treating acute kidney injury. In certain embodiments, the acute kidney injury is contrast-induced acute kidney injury. In some embodiments, the device comprises a catheter, a position indication means on the catheter, and a flow disturbing means retractable into the catheter wherein the flow disturbing means is positioned at suprarenal aorta to provide blood flow disturbance which makes a contrast media become diluted before taking into the renal arteries carrying by a disturbed blood flow distributing back to the infra-renal aorta. In some embodiments, the device comprises a balloon catheter having a first balloon, a second balloon and at least one sensor associated with the second balloon. In certain embodiments, the device comprises two sensors described herein. In certain embodiments, the balloon catheter further comprises a side aperture for infusing normal saline or medication.

Although preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein can be employed in practicing the invention. It is intended that the following claims define the scope of the invention and that methods and structures within the scope of these claims and their equivalents be covered thereby.

What is claimed is:

1. A method of preventing acute kidney injury from contrast agent introduced into vasculature of a subject, the method comprising:
    positioning a catheter device in an abdominal aorta of the subject adjacent renal artery ostia of the subject;
    deploying an occlusive element of the catheter device to occlude the renal artery ostia;
    introducing a bolus of the contrast agent into the abdominal aorta of the subject while the occlusive element is deployed and occluding the renal artery ostia to prevent the contrast agent from entering into renal arteries of the subject; and
    collapsing the occlusive element after the bolus of the contrast agent has been introduced to allow blood flow to the renal arteries to resume.

2. The method of claim 1, further comprising repeating the steps of deploying the occlusive element to occlude the renal artery ostia, introducing the bolus of the contrast agent while the occlusive element is deployed and occluding the renal artery ostia, and collapsing the occlusive element after the bolus of the contrast agent has been introduced.

3. The method of claim 1, wherein at least a portion of the catheter device is radio-opaque and further comprising tracking the position of the catheter device as the catheter device is positioned.

4. The method of claim 1, wherein the occlusive element comprises at least one inflatable balloon.

5. The method of claim 4, wherein the at least one inflatable balloon comprises a first balloon and a second balloon.

6. The method of claim 5, wherein the first and second inflatable balloons are disposed bilaterally with respect to one another to occlude a first renal ostium and a second renal ostium, respectively, when inflated.

7. The method of claim 5, wherein the first and second inflatable balloons are disposed about a central shaft of the catheter device.

8. The method of claim 5, wherein catheter device comprises at least one connection tube for connecting one or more of the first or second inflatable balloon to an inflation fluid lumen of the catheter device, the inflation fluid lumen providing fluid to inflate the first or second balloon.

9. The method of claim 5, wherein the expanded first and second balloons allow blood flow along the catheter device.

10. The method of claim 1, further comprising measuring pressure with a sensor coupled to the occlusive element of the catheter device.

11. The method of claim 1, wherein positioning the catheter device in the abdominal aorta of the subject comprises advancing the catheter device through one or more of a femoral artery, a brachial artery, or a radial artery.

12. The method of claim 1, further comprising introducing into the abdominal aorta the bolus of the contrast agent through an infusion port of the catheter shaft.

* * * * *